(12) United States Patent
Meroueh et al.

(10) Patent No.: US 11,999,720 B2
(45) Date of Patent: Jun. 4, 2024

(54) PYRAZOLYLACYLPYRAZOLINE COMPOUNDS AND METHOD FOR TREATING PAIN

(71) Applicants: THE TRUSTEES OF INDIANA UNIVERSITY, Bloomington, IN (US); THE UNITED STATES GOVERNMENT AS REPRESENTED BY THE DEPARTMENT OF VETERANS AFFAIRS, Washington, DC (US)

(72) Inventors: Samy Meroueh, Carmel, IN (US); Fletcher A. White, Indianapolis, IN (US); Alexander G. Obukhov, Carmel, IN (US)

(73) Assignees: THE TRUSTEES OF INDIANA UNIVERSITY, Bloomington, IN (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 288 days.

(21) Appl. No.: 17/251,473

(22) PCT Filed: Sep. 19, 2019

(86) PCT No.: PCT/US2019/051920
§ 371 (c)(1),
(2) Date: Dec. 11, 2020

(87) PCT Pub. No.: WO2020/061303
PCT Pub. Date: Mar. 26, 2020

(65) Prior Publication Data
US 2021/0155609 A1 May 27, 2021

Related U.S. Application Data

(60) Provisional application No. 62/733,153, filed on Sep. 19, 2018.

(51) Int. Cl.
*C07D 401/14* (2006.01)
*C07D 403/04* (2006.01)
*C07D 403/14* (2006.01)

(52) U.S. Cl.
CPC ......... *C07D 403/04* (2013.01); *C07D 401/14* (2013.01); *C07D 403/14* (2013.01)

(58) Field of Classification Search
CPC ... C07D 401/14; C07D 403/04; C07D 403/14
See application file for complete search history.

(56) References Cited

U.S. PATENT DOCUMENTS

| | | |
|---|---|---|
| 2013/0028989 A1 | 1/2013 | Turchi et al. |
| 2014/0323483 A1 | 10/2014 | Goguen |
| 2017/0182055 A1 | 6/2017 | Turchi et al. |

FOREIGN PATENT DOCUMENTS

| | | |
|---|---|---|
| WO | 2018/001973 A1 | 1/2018 |

OTHER PUBLICATIONS

PCT International Search Report and Written Opinion completed by the ISA/US dated Octr. 30, 2019 and issued in connection with PCT/US2019/051920.
Xingjuan Chen et al: "Small-molecule Ca V α1 δ;Ca V β antagonist suppresses neuronal voltage-gated calcium-channel trafficking", Proceedings of the National Academy of Sciences, vol. 115, No. 45, Oct. 24, 2018 (Oct. 24, 2018), pp. E10566-E10575.
Shuck S.C . et al. Targeted inhibition of Replication Protein A reveals cytotoxic activity, synergy with chemotherapeutic DNA-damaging agents, and insight into cellular function. Cancer Res. 2010, 70(8), pp. 3189-3198. doi. 10.1158/0008-5472.CAN-09-3422.

*Primary Examiner* — Brian E McDowell
(74) *Attorney, Agent, or Firm* — Barnes & Thornburg LLP

(57) ABSTRACT

This invention relates to pyrazolylacylpyrazoline compounds or pharmaceutically acceptable salts thereof, and for the use of the compounds to treat neurological disorders.

12 Claims, 7 Drawing Sheets

PYRAZOLYLACYLPYRAZOLINE COMPOUNDS AND METHOD FOR TREATING PAIN

CROSS REFERENCE TO RELATED APPLICATIONS

This application is a U.S. national stage entry of PCT Application No. PCT/US2019/051920, filed Sep. 18, 2019, which claims the benefit under 35 U.S.C. § 119(e) of U.S. Provisional Application No. 62/733,153, filed on Sep. 19, 2018, the disclosures of each of which are hereby incorporated by reference in their entireties.

GOVERNMENT RIGHTS

This invention was made with government support under HL115140 and TR001108 awarded by National Institutes of Health. The government has certain rights in the invention.

BACKGROUND

In the central nervous system, voltage-gated calcium channels play important and diverse roles in the synaptic transmission of electrical signals (e.g., neurotransmitter release), in the integration and modulation of these signals, and in the transduction of membrane depolarization into intracellular signals. To accomplish these diverse functions, neurons express a variety of calcium channels that are composed of large heteromeric assemblies of pore forming α1 (CaVα1) subunits and auxiliary subunits. Among the auxiliary subunits of voltage-gated calcium channels, CaVβ increase the surface expression of voltage-gated calcium channels and regulate their biophysical properties. The interaction between pore and auxiliary subunits is driven by protein-protein interactions. One such interaction between pore and auxiliary subunits of a voltage-gated ion channel is a tight CaVα1●CaVβ protein-protein interaction.

Pain is a prevalent problem. Pain can arise from or accompany a wide variety of diseases and disease states. Clinically-approved blockers of voltage-gated calcium channels for pain management are encumbered by numerous off-target effects and exhibit narrow therapeutic windows. A need remains for compounds to treat pain that are both non-addictive and avoid the other drawbacks of existing pain medicines.

SUMMARY

In one aspect, the disclosure relates to a compound of the Formula (1)

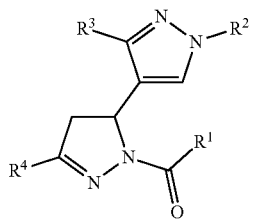

(1)

wherein $R^1$ is selected from the group consisting of —($C_1$-$C_4$ alkyl)-$CO_2H$, —$CO_2H$ and tetrazole substituted phenyl; $R^2$ is selected from the group consisting of phenyl, methoxy substituted phenyl and pyridinyl; $R^3$ is selected from the group consisting of ($C_1$-$C_3$ alkyl) substituted phenyl halo substituted phenyl; and $R^4$ is selected from the group consisting of alkoxy substituted phenyl and phenyl substituted pyridine; or a pharmaceutically acceptable salt thereof.

In another aspect, the disclosure relates to a compound of the Formula (1a)

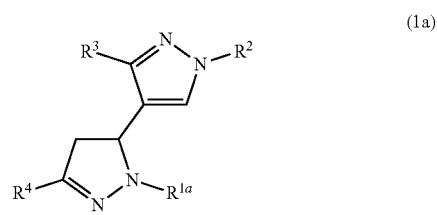

(1a)

wherein
$R^1$ is $C(O)R^1$ or phenyl optionally substituted with one or more —$CO_2H$, —$C(O)OC_1$-$C_4$ alkyl, or heteroaryl, wherein R is —$C_1$-$C_4$ alkyl-$CO_2H$, —$C_1$-$C_4$ alkyl-$C(O)OC_1$-$C_4$ alkyl, or phenyl, wherein each hydrogen atom in phenyl is independently optionally substituted with —$CO_2H$, —$C(O)OC_1$-$C_4$ alkyl, or heteroaryl;
$R^2$ is phenyl, heteroaryl, —$C_1$-$C_4$ alkyl-phenyl, or —$C_1$-$C_4$ alkyl, wherein each hydrogen atom in phenyl is independently optionally substituted with —$C_1$-$C_4$ alkoxy;
$R^3$ is phenyl, wherein each hydrogen atom in phenyl is independently optionally substituted with —$C_1$-$C_3$ alkyl, halo, —$C_1$-$C_4$ alkoxy, or heteroaryl; and
$R^4$ is phenyl, wherein each hydrogen atom in phenyl is independently optionally substituted with $C_1$-$C_4$ alkoxy, piperazinyl, or heteroaryl;
with the proviso that the compound of Formula (1a) is not

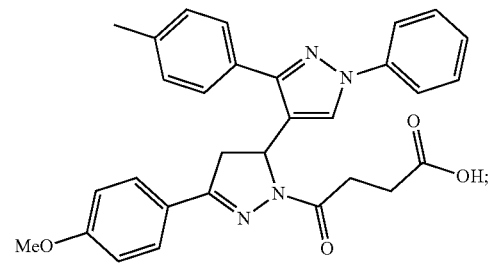

or a pharmaceutically acceptable salt thereof.

In another aspect, the disclosure relates to a pharmaceutical composition comprising a compound of Formula (1) or Formula (1a), or a pharmaceutically acceptable salt thereof, and at least one of a pharmaceutically acceptable carrier, diluent or excipient.

In another aspect, the disclosure relates a method to treat a neurological disorder in a mammal in need thereof, comprising administering an effective amount of a compound, or a pharmaceutically acceptable salt thereof of a compound of Formula (1) or Formula (1a).

In another aspect, the disclosure relates to a method to modulate a protein-protein interaction between pore and auxiliary subunits of a voltage-gated ion channel in a nerve cell, comprising contacting the nerve cell with an effective amount of the compound of Formula (1) or Formula (1a).

Additional embodiments, features, and advantages of the disclosure will be apparent from the following detailed description and through practice of the disclosure.

BRIEF DESCRIPTION OF THE DRAWINGS

FIG. 8 shows the average current-voltage relationships acquired during voltage ramps for each test group. FIG. 9 shows the average G-V curves for each treatment group. The gray vertical lines are the error bars (S.E.M.).

FIG. 10 shows the average G-V curves before and after 5-minute incubation with DMSO (p>0.05). FIG. 11 shows the average G-V curves before and after 5-minute incubation with 14 (BTT-369, p<0.01). The gray vertical lines are the error bars (S.E.M.). "ns"—stands for not significant.

DETAILED DESCRIPTION

Figure 1:
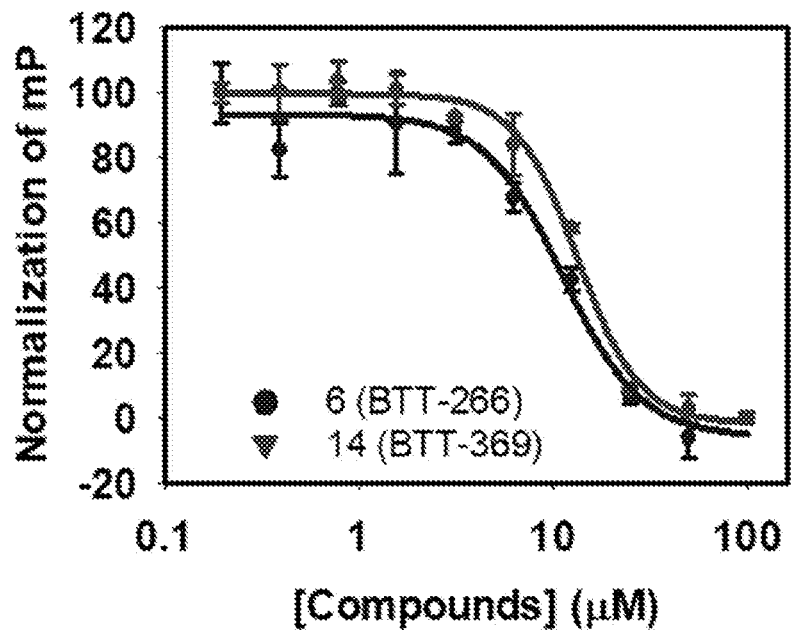
FIG. 1 shows a fluorescence polarization assay used to determine an inhibition constant for compounds 6 and 14.
Figure 2:
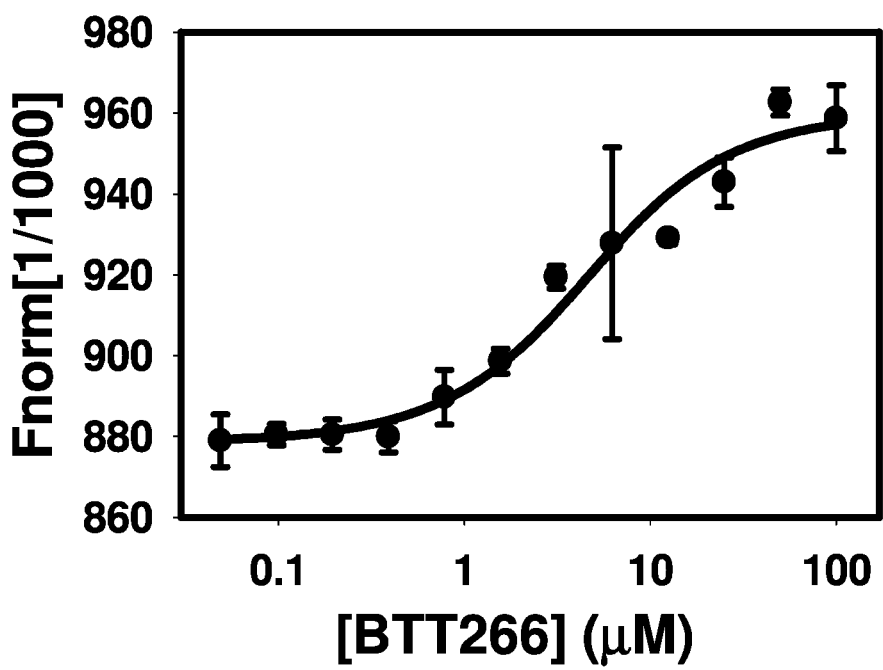
FIG. 2 shows a binding curve that emerged from the use of microscale thermophoresis to establish direct binding of compound 6. Curve fitting analysis led to a dissociation constant of 3.6±1.1 µM.
Figure 3:
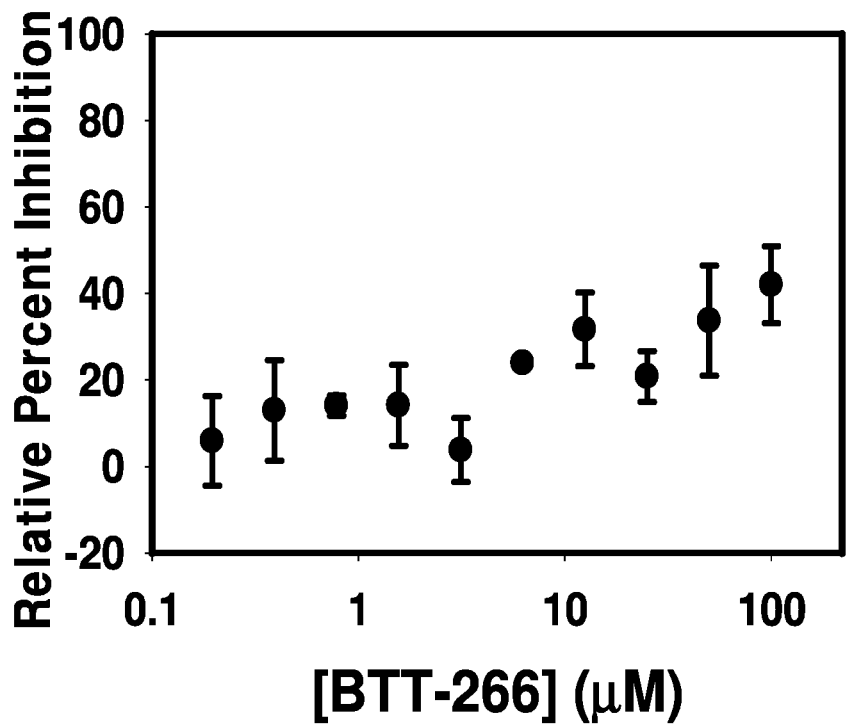
FIG. 3 shows compound 6 does not inhibit the protein-protein interaction between $Ca_V\beta_3$ Arg-307-Ala as evidenced by a lack of displacement of fluorescently-labeled $Ca_V\alpha_{1-AID}$ bound to the mutated $Ca_V\beta_3$.
Figure 4:
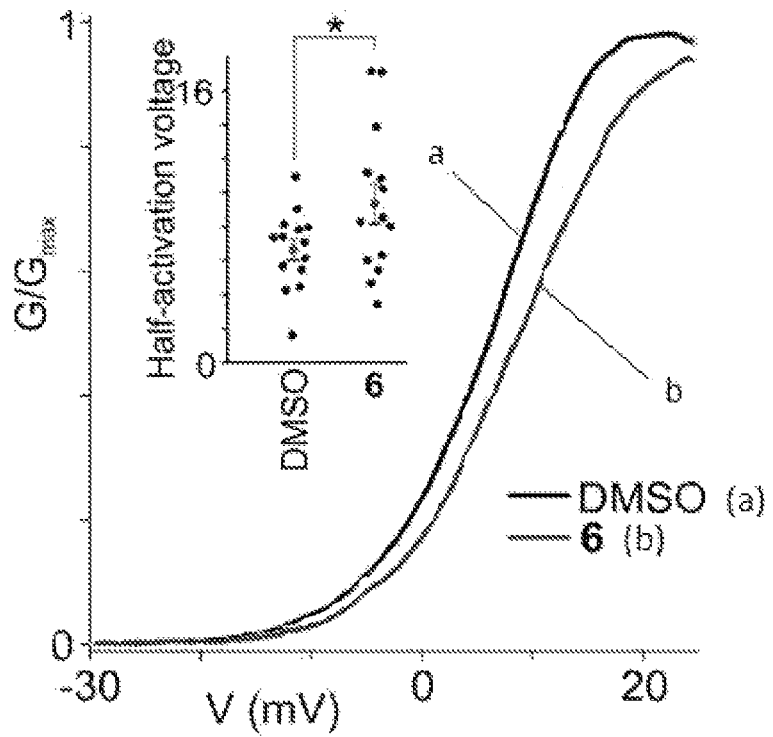
FIG. 4 shows the effect of 6 on the voltage dependence of activation of $Ca_V2.2$ channels in HEK-$Ca_V2.2$ cells pretreated with the vehicle or the indicated compounds for 48 hours. The G-V curves are shown. The inset shows a comparison of half-activation potentials in DMSO and 50 µM 6 pretreated HEK-$Ca_V2.2$ cells (48 hours).
Figure 5:
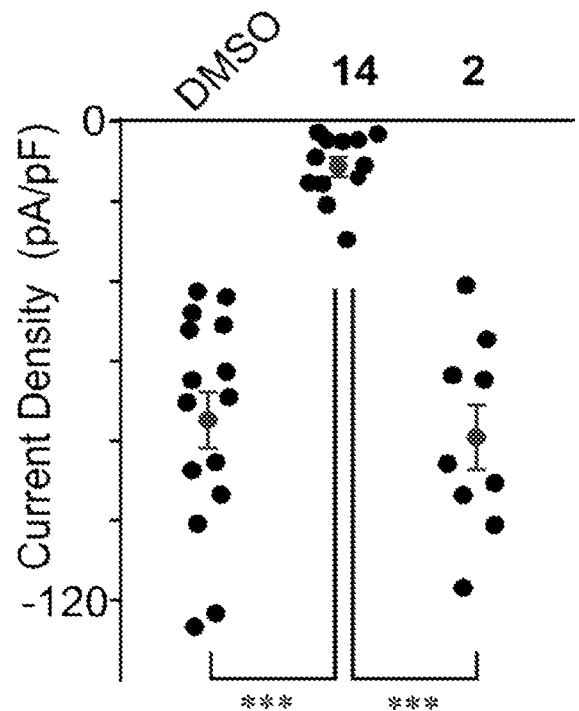
FIG. 5 shows the $Ca_V2.2$ current densities in HEK-$Ca_V2.2$ cells pretreated for 48 hours with either DMSO (n=15), 14 (BTT-369, n=12), or 2 (BTT-245, n=9). *** corresponds to p<0.001.
Figure 6:
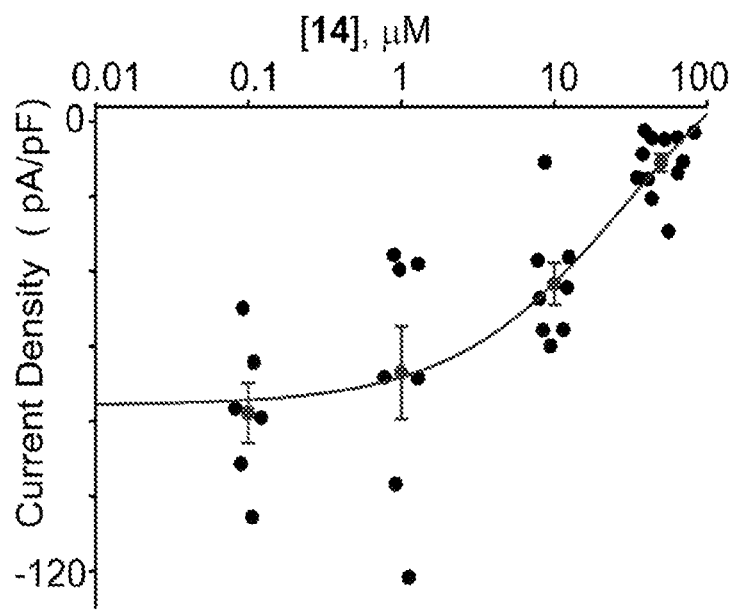
FIG. 6 shows the concentration-effect curve for 14 (BTT-369). HEK-$Ca_V2.2$ cells were pretreated with various concentrations of compound 14 for 48 hours. $Ca_V2.2$ currents were acquired during 20-ms depolarizing pulses, and the current densities were calculated as a ratio of the peak current amplitude and each cell capacitance (0.1 µM, n=6; 1 µM, n=7; 10 µM, n=8; 50 µM, n=12). The line is the fit of the data to the four-parameter logistic function. The apparent $IC_{50}$ value is 31 µM.
Figure 7:
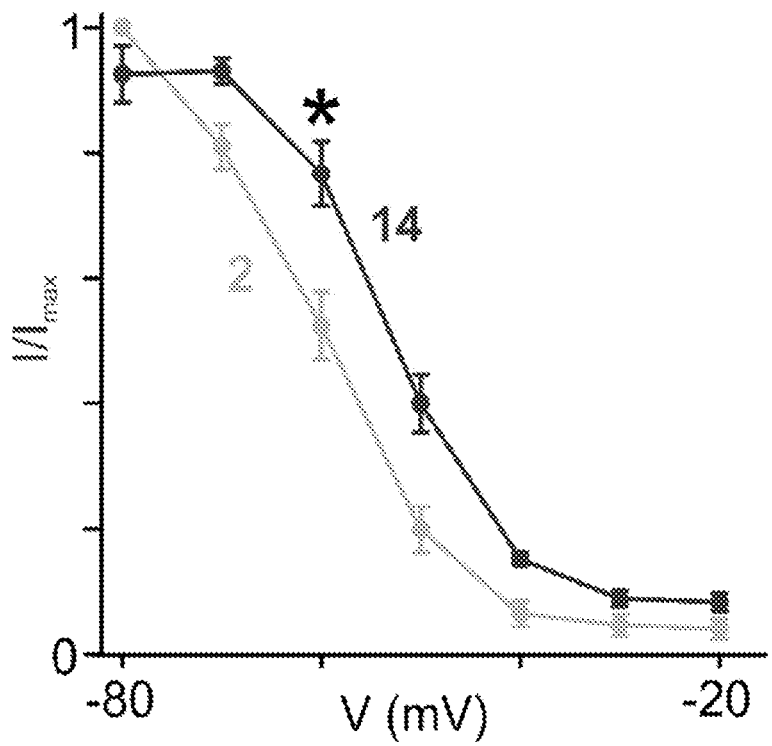
FIG. 7 shows the effect of 2 (BTT-245) and 14 (BTT369) on the voltage dependence of the steady-state inactivation of $Ca_V2.2$ channels. EK-$Ca_V2.2$ cells were pretreated with the indicated compounds for 48 hours. *** corresponds to p<0.05.
Figure 8:
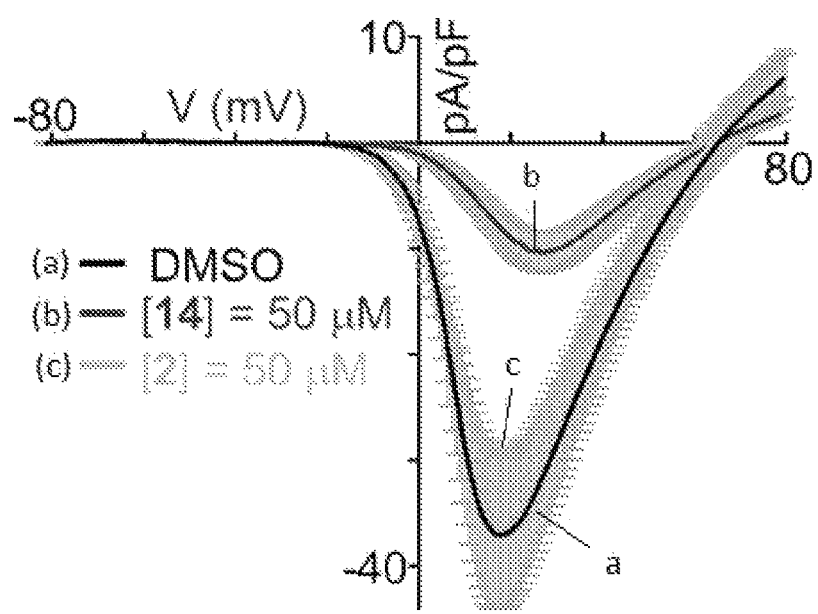
FIGS. 8 and 9 show the effects of 2 and 14 on the voltage dependence of activation of $Ca_V2.2$ channels in HEK-$Ca_V2.2$ cells pretreated with the vehicle or the indicated compounds for 48 hours.
Figure 9:
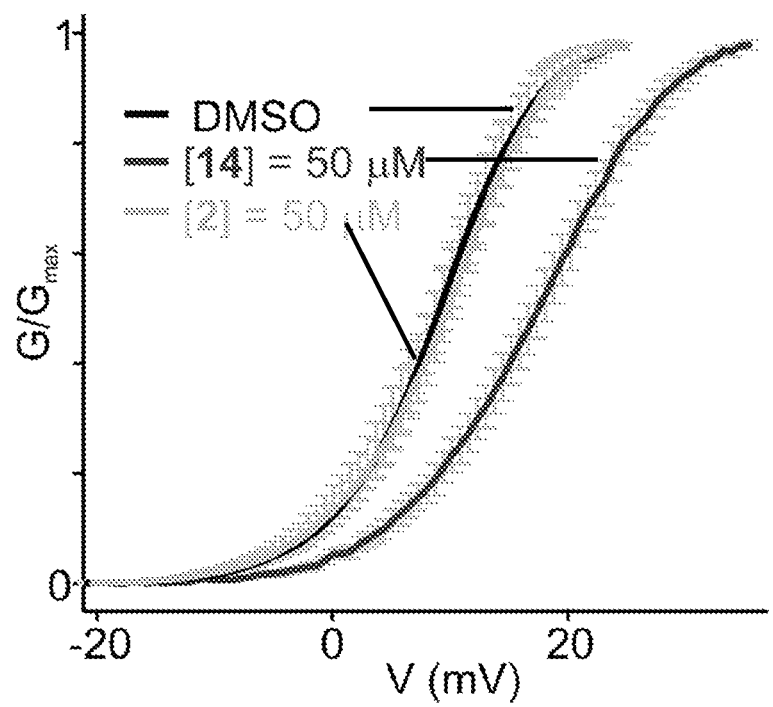
Figure 10:
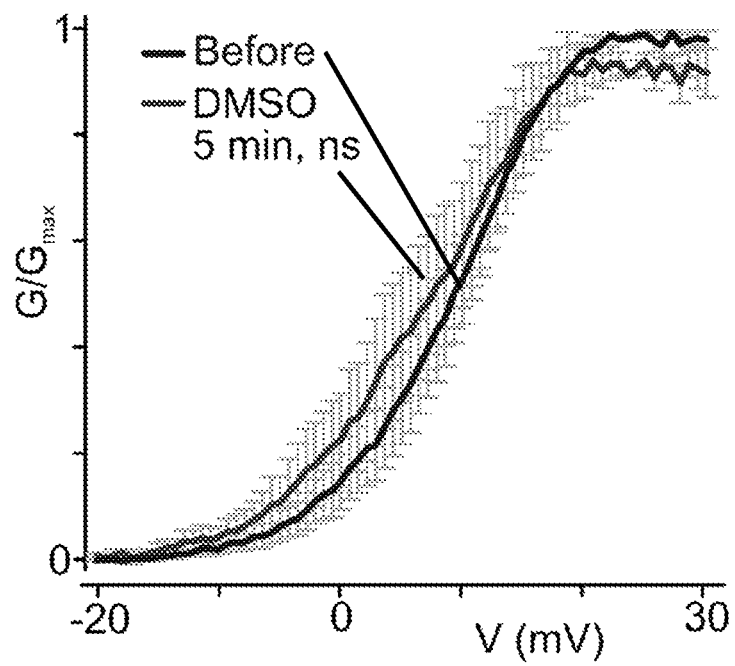
FIGS. 10 and 11 show acute effects of DMSO and 14 on the voltage dependence of activation of $Ca_V2.2$ channels in HEK-$Ca_V2.2$ cells.
Figure 11:
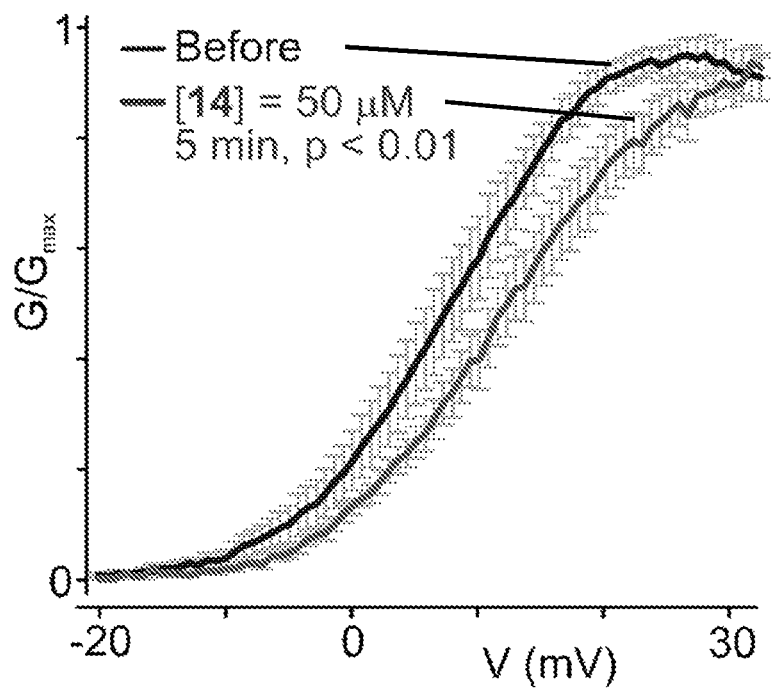
Figure 12:
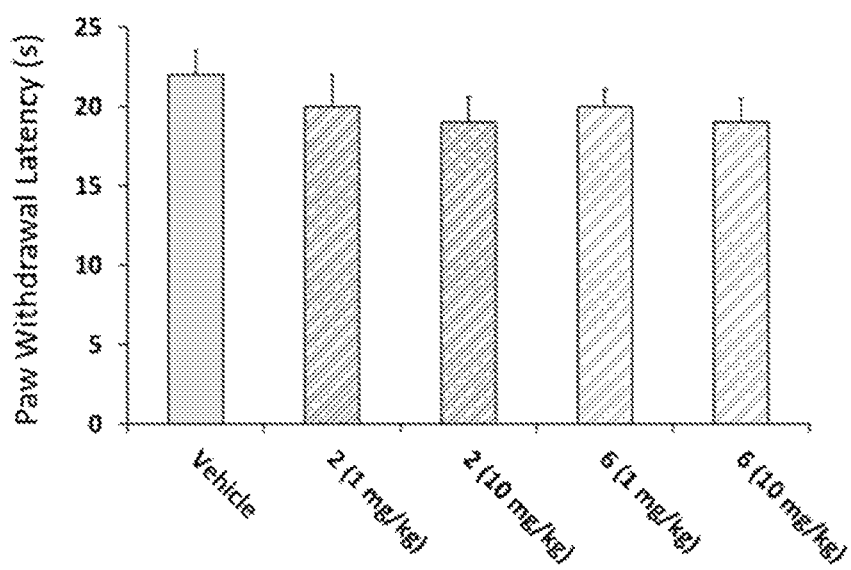
FIG. 12 shows a bar graph of paw withdrawal latency (PWL, in seconds) of rats (n=6 per group) demonstrating a lack of analgesic effect for compound 2 or 6.
Figure 13:
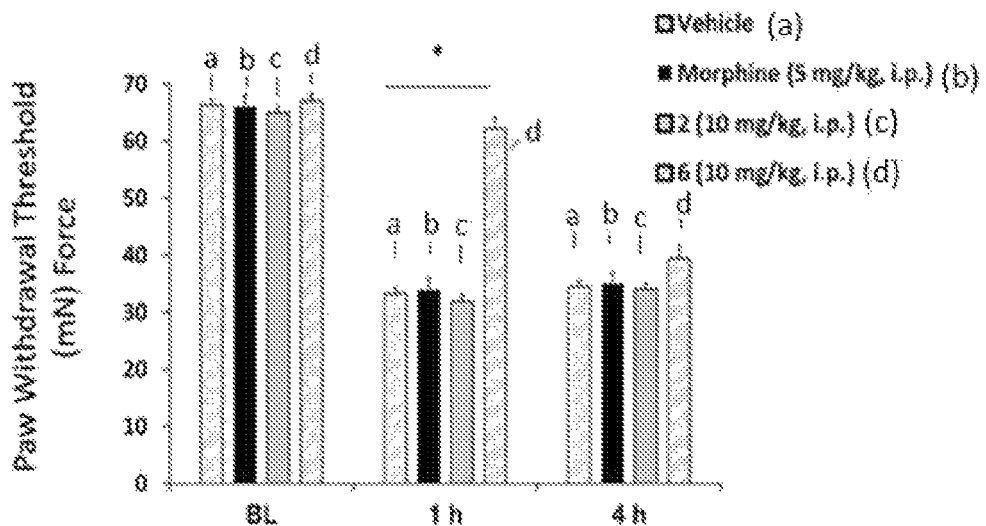
FIG. 13 shows withdrawal threshold (in milli-Newtons, mN) in response to von Frey stimulation to the paw ipsilateral to injury following a single, intraperitoneal administration of vehicle, morphine (5 mg/kg), compound 2, or compound 6 (10 mg/kg, n=8) at 4 weeks after TNI. The ability of 6 (striped bar) to reverse TNI-induced mechanical hypersensitivity was significantly different from both 2 (solid grey bar) and morphine-treated animals (black striped bar). (*p<0.05 versus 2 and morphine-treated TNI rodents (mean±SE; n=8, repeated measures ANOVA with Tukey post-hoc).
Figure 14:
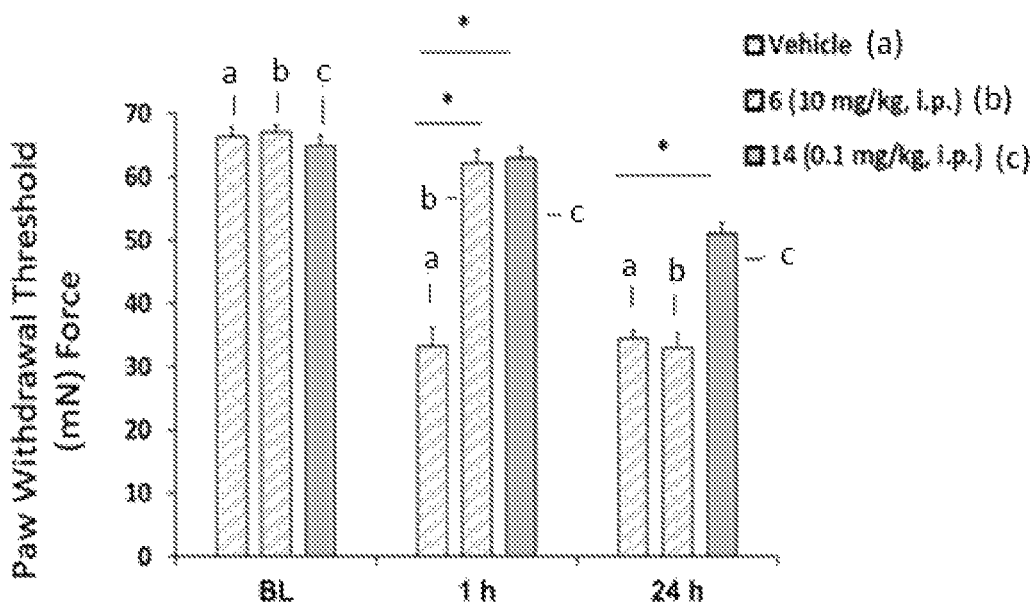
FIG. 14 shows at 4 weeks, a single bolus injection of compound 14 (0.1 mg/kg) significantly reversed mechanical hypersensitivity at both 1 and 24 h post-dosing. For comparison, 6 (10 mg/kg) reversal of mechanical hypersensitivity was limited to 1 h (*p<0.05 versus 6 and vehicle-treated TNI rodents (mean±SE; n=8, repeated measures ANOVA with Tukey post-hoc).

Before the present disclosure is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as is commonly understood by one of ordinary skill in the art to which this disclosure belongs. All patents, applications, published applications and other publications referred to herein are incorporated by reference in their entireties. If a definition set forth in this section is contrary to or otherwise inconsistent with a definition set forth in a patent, application, or other publication that is herein incorporated by reference, the definition set forth in this section prevails over the definition incorporated herein by reference.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As used herein, the terms "including," "containing," and "comprising" are used in their open, non-limiting sense.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Chemical nomenclature for compounds described herein has generally been derived using the commercially-available ACD/Name 2014 (ACD/Labs) or ChemBioDraw ultra 13.0 (Perkin Elmer).

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Definitions

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_9$, $C_1$-$C_8$, $C_1$-$C_7$, $C_1$-$C_6$, $C_1$-$C_4$, and $C_1$-$C_3$. Illustratively, such particularly limited length alkyl groups, including $C_1$-$C_8$, $C_1$-$C_7$, $C_1$-$C_6$, $C_1$-$C_4$, and $C_1$-$C_3$ and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like. Illustrative examples of heteroaryl groups shown in graphical representations, include the following entities, in the form of properly bonded moieties:

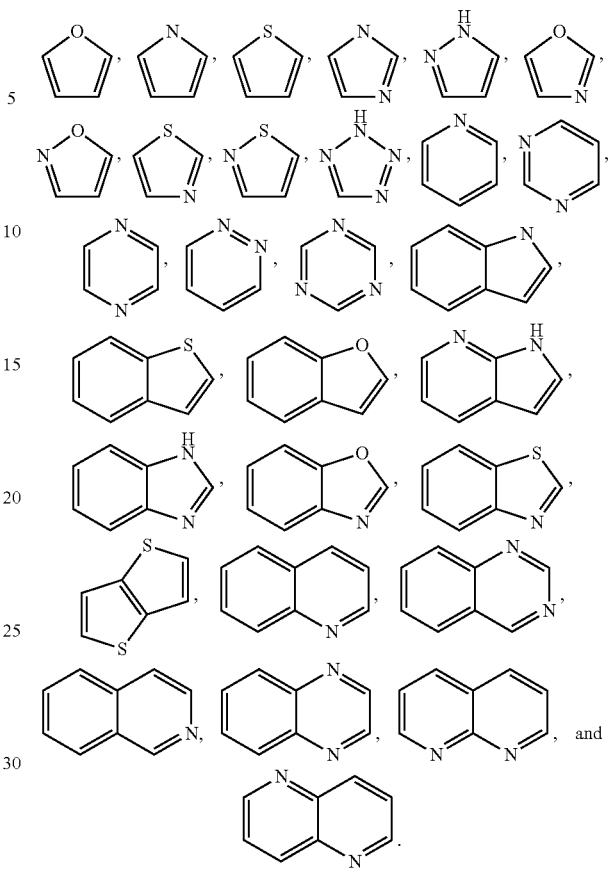

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "halo" or "halogen" refers to fluorine, chlorine, bromine, or iodine.

As used herein, "bond" refers to a covalent bond.

The term "substituted" means that the specified group or moiety bears one or more substituents. The term "unsubstituted" means that the specified group bears no substituents. Where the term "substituted" is used to describe a structural system, the substitution is meant to occur at any valency-allowed position on the system. In some embodiments, "substituted" means that the specified group or moiety bears one, two, or three substituents. In other embodiments, "substituted" means that the specified group or moiety bears one or two substituents. In still other embodiments, "substituted" means the specified group or moiety bears one substituent.

As used herein, "optional" or "optionally" means that the subsequently described event or circumstance may but need not occur, and that the description includes instances where the event or circumstance occurs and instances in which it does not. For example, "wherein each hydrogen atom in phenyl is independently optionally substituted by $CO_2H$" means that a $CO_2H$ may be but need not be present on phenyl by replacement of a hydrogen atom for each $CO_2H$ group, and the description includes situations where phenyl is not substituted with the $CO_2H$ group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, the term "pharmaceutically acceptable salt" refers to those salts which counter ions which may be used in pharmaceuticals. See, generally, S. M. Berge, et al., "Pharmaceutical Salts," J. Pharm. Sci., 1977, 66, 1-19. Preferred pharmaceutically acceptable salts are those that are pharmacologically effective and suitable for contact with the tissues of subjects without undue toxicity, irritation, or allergic response. A compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt. Such salts include:

(1) acid addition salts, which can be obtained by reaction of the free base of the parent compound with inorganic acids such as hydrochloric acid, hydrobromic acid, nitric acid, phosphoric acid, sulfuric acid, and perchloric acid and the like, or with organic acids such as acetic acid, oxalic acid, (D) or (L) malic acid, maleic acid, methane sulfonic acid, ethanesulfonic acid, p-toluenesulfonic acid, salicylic acid, tartaric acid, citric acid, succinic acid or malonic acid and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, trimethamine, N-methylglucamine, and the like.

Pharmaceutically acceptable salts are well known to those skilled in the art, and any such pharmaceutically acceptable salt may be contemplated in connection with the embodiments described herein. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of Formula (1) or Formula (1a) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

The disclosure also relates to pharmaceutically acceptable prodrugs of the compounds of Formula (1) and Formula (1a) and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (1) and Formula (1a). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

The present disclosure also relates to pharmaceutically active metabolites of compounds of Formula (1) and Formula (1a), and uses of such metabolites in the methods of the disclosure. A "pharmaceutically active metabolite" means a pharmacologically active product of metabolism in the body of a compound of Formula (1) and Formula (1a), or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sci. 1997, 86 (7), 765-767; Bagshawe, Drug Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula depicted herein is intended to represent a compound of that structural formula as well as certain variations or forms. For example, a formula given herein is intended to include a racemic form, or one or more enantiomeric, diastereomeric, or geometric isomers, or a mixture thereof. Additionally, any formula given herein is intended to refer also to a hydrate, solvate, or polymorph of such a compound, or a mixture thereof. For example, it will be appreciated that compounds depicted by a structural formula containing the symbol "⌇" include both stereoisomers for the carbon atom to which the symbol "⌇" is attached, specifically both the bonds "▬" and "⦀" are encompassed by the meaning of "⌇". For example, in some exemplary embodiments, certain compounds provided herein can be described by the formula

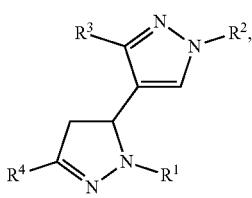

which formula will be understood to encompass compounds having both stereochemical configurations at the relevant carbon atom, specifically in this example

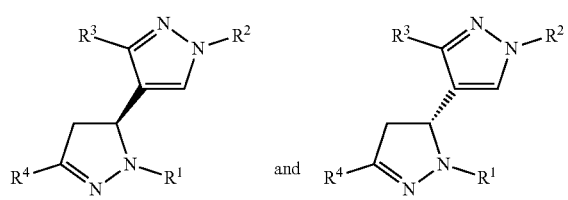

and other stereochemical combinations.

Compounds of Formula (1) and Formula (1a) wherein the chiral center at the core pyrazoline ring are in the S-configuration are further preferred. Although the present invention contemplates all individual enantiomers and diastereomers, as well as mixtures of the enantiomers of the compounds, including racemates, the compounds with the absolute configuration as set forth below are particularly preferred.

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$ $^{35}S$, $^{18}F$, $^{36}Cl$, and $^{125}I$, respectively. Such isotopically labelled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second substituted member and B attached to the first substituted member.

REPRESENTATIVE EMBODIMENTS

In some embodiments, compounds described herein comprise a compound of the Formula (1a)

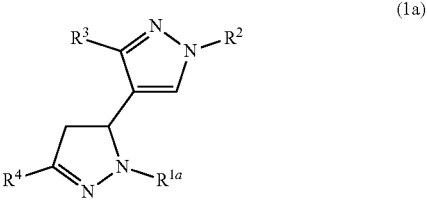

(1a)

or a pharmaceutical acceptable salt thereof.

In some embodiments, compounds described herein comprise a compound the Formula (1)

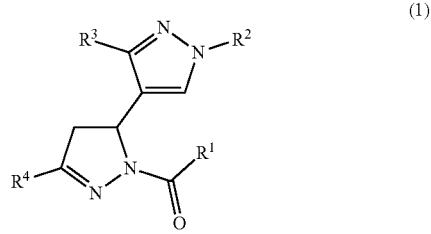

(1)

or a pharmaceutical acceptable salt thereof.

In some embodiments, Ria is $C(O)R^1$ or phenyl wherein each hydrogen atom in phenyl is independently optionally substituted with —$CO_2H$, —$C(O)OC_1$-$C_4$ alkyl, or heteroaryl. In some embodiments, $R^1$ is —$C_1$-$C_4$ alkyl-$CO_2H$, —$C_1$-$C_4$ alkyl-$C(O)OC_1$-$C_4$ alkyl, or phenyl, wherein each hydrogen atom in phenyl is independently optionally substituted with —$CO_2H$, —$C(O)OC_1$-$C_4$ alkyl, or heteroaryl. In some embodiments, $R^1$ is selected from the group consisting of ($C_1$-$C_4$ alkyl)-$CO_2H$ and $CO_2H$ and tetrazole substituted phenyl. In some embodiments, $R^1$ is selected from the group consisting of $CO_2H$ substituted phenyl, tetrazole substituted phenyl, and $(CH_2)_2CO_2H$. In some embodiments, $R^1$ is $(CH_2)_2CO_2H$.

In some embodiments, $R^2$ is phenyl, heteroaryl, $C_1$-$C_4$ alkyl-phenyl, or $C_1$-$C_4$ alkyl, wherein each hydrogen atom in phenyl is independently optionally substituted with $C_1$-$C_4$ alkoxy. In some embodiments, $R^2$ is selected from the group consisting of phenyl, methoxy substituted phenyl, and pyridinyl. In some embodiments, $R^2$ is phenyl, methoxy substituted phenyl, or heteroaryl. In some embodiments, $R^2$ is phenyl. In some embodiments, $R^2$ is methoxy substituted phenyl.

In some embodiments, $R^3$ is phenyl, wherein each hydrogen atom in phenyl is independently optionally substituted with —$C_1$-$C_3$ alkyl, halo, —$C_1$-$C_4$ alkoxy, or heteroaryl. In some embodiments, $R^3$ is selected from the group consisting of ($C_1$-$C_3$ alkyl) substituted phenyl and halo substituted phenyl. In some embodiments, $R^3$ is methyl-phenyl or chloro-phenyl.

In some embodiments, $R^4$ is phenyl, wherein each hydrogen atom in phenyl is independently optionally substituted with $C_1$-$C_4$ alkoxy, piperazinyl, or heteroaryl. In some embodiments, $R^4$ is selected from the group consisting of alkoxy substituted phenyl and phenyl substituted pyridyl. In some embodiments, $R^4$ is methoxy-phenyl or phenyl pyridyl.

In some illustrative embodiments, a compound of Formula (1) or Formula (1a) is not

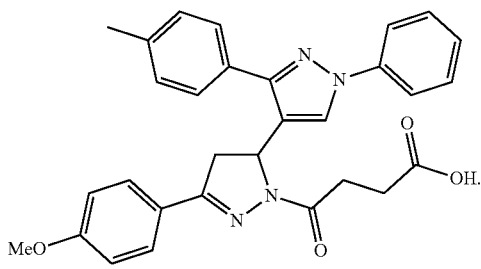

The following represent illustrative embodiments of compounds of the Formula (1) and Formula (1a):

| Compound | Structure | Name |
|---|---|---|
| 1 | 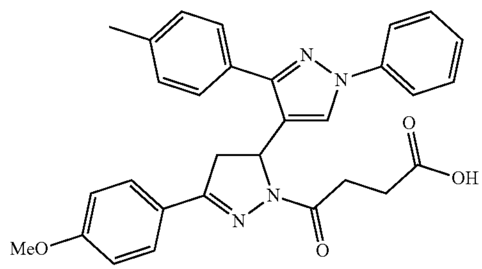 [SMILES: COc1ccc(C2=NN(C(=O)CCC(=O)O)C(c3cn(-c4ccccc4)nc3-c3ccc(C)cc3)C2)cc1] | 4-(5'-(4-methoxyphenyl)-1-phenyl-5-(p-tolyl)-3',4'-dihydro-1H,2'H-[3,3'-bipyrazol]-2'-yl)-4-oxobutanoic acid |
| 2 | 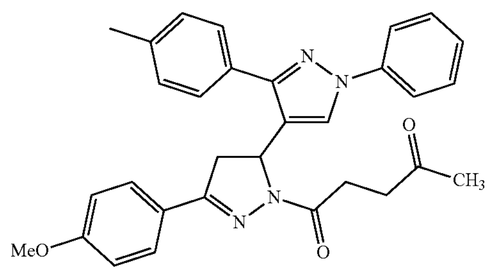 [SMILES: COc1ccc(C2=NN(C(=O)CCC(C)=O)C(c3cn(-c4ccccc4)nc3-c3ccc(C)cc3)C2)cc1] | 1-(5-(4-methoxyphenyl)-1'-phenyl-3'-(p-tolyl)-3,4-dihydro-1'H,2H-[3,4'-bipyrazol]-2-yl)pentane-1,4-dione |
| 3 | 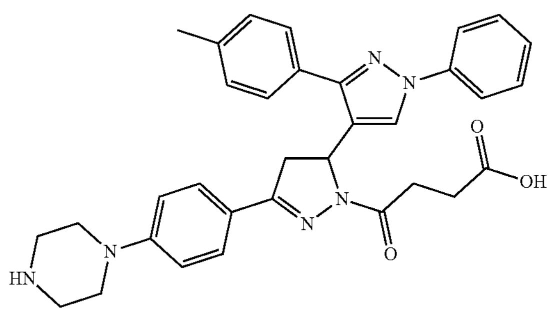 [SMILES: Cc1ccc(-c2nn(-c3ccccc3)cc2C2CC(c3ccc(N4CCNCC4)cc3)=NN2C(=O)CCC(=O)O)cc1] | 4-oxo-4-(1'-phenyl-5-(4-(piperazin-1-yl)phenyl)-3'-(p-tolyl)-3,4-dihydro-1'H,2H-[3,4'-bipyrazol]-2-yl)butanoic acid |
| 4 | 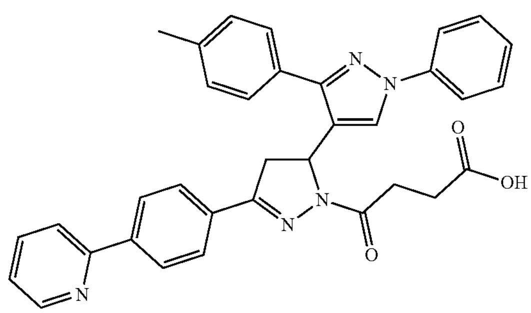 [SMILES: Cc1ccc(-c2nn(-c3ccccc3)cc2C2CC(c3ccc(-c4ccccn4)cc3)=NN2C(=O)CCC(=O)O)cc1] | 4-oxo-4-(1'-phenyl-5-(4-(pyridin-2-yl)phenyl)-3'-(p-tolyl)-3,4-dihydro-1'H,2H-[3,4'-bipyrazol]-2-yl)butanoic acid |

-continued

| Compound | Structure | Name |
|---|---|---|
| 5 | 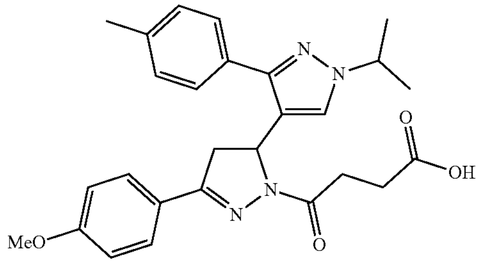 [SMILES: COc1ccc(C2=NN(C(=O)CCC(=O)O)C(c3cn(C(C)C)nc3-c3ccc(C)cc3)C2)cc1] | 4-(1'-isopropyl-5-(4-methoxyphenyl)-3'-(p-tolyl)-3,4-dihydro-1'H,2H-[3,4'-bipyrazol]-2-yl)-4-oxobutanoic acid |
| 6 | 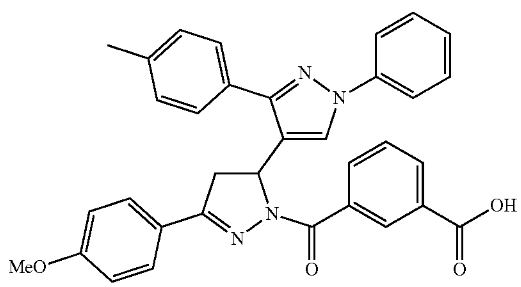 [SMILES: COc1ccc(C2=NN(C(=O)c3cccc(C(=O)O)c3)C(c3cn(-c4ccccc4)nc3-c3ccc(C)cc3)C2)cc1] | 3-(5-(4-methoxyphenyl)-1'-phenyl-3'-(p-tolyl)-3,4-dihydro-1'H,2H-[3,4'-bipyrazole]-2-carbonyl)benzoic acid |
| 7 | 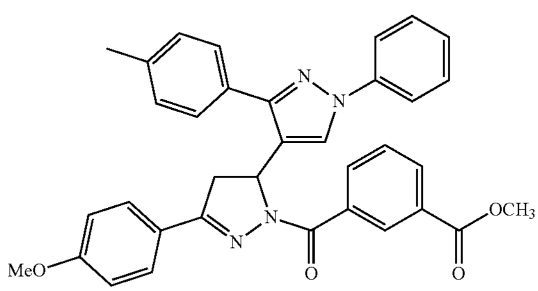 [SMILES: COC(=O)c1cccc(C(=O)N2N=C(c3ccc(OC)cc3)CC2c2cn(-c3ccccc3)nc2-c2ccc(C)cc2)c1] | methyl 3-(5-(4-methoxyphenyl)-1'-phenyl-3'-(p-tolyl)-3,4-dihydro-1'H,2H-[3,4'-bipyrazole]-2-carbonyl)benzoate |
| 8 | 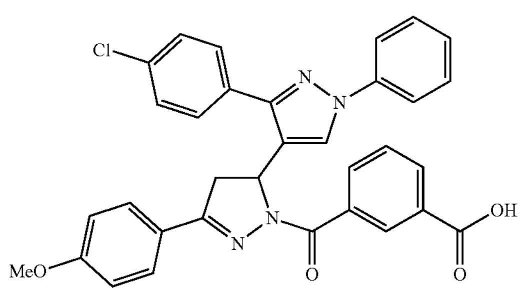 | 3-(3'-(4-chlorophenyl)-5-(4-methoxyphenyl)-1'-phenyl-3,4-dihydro-1'H,2H-[3,4'-bipyrazole]-2-carbonyl)benzoic acid |
| 9 | 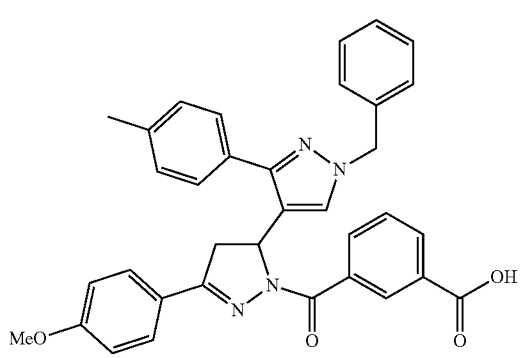 [SMILES: COc1ccc(C2=NN(C(=O)c3cccc(C(=O)O)c3)C(c3cn(Cc4ccccc4)nc3-c3ccc(C)cc3)C2)cc1] | 3-(1'-benzyl-5-(4-methoxyphenyl)-3'-(p-tolyl)-3,4-dihydro-1'H,2H-[3,4'-bipyrazole]-2-carbonyl)benzoic acid |

-continued

| Compound | Structure | Name |
|---|---|---|
| 10 | 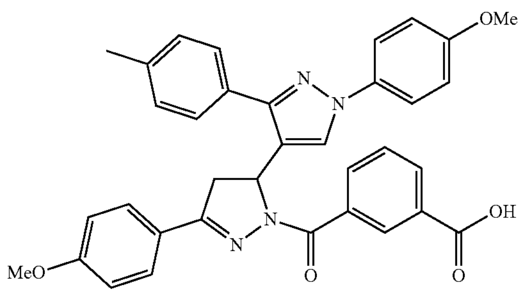 [SMILES: COc1ccc(C2=NN(C(=O)c3cccc(C(=O)O)c3)C(c3cn(-c4ccc(OC)cc4)nc3-c3ccc(C)cc3)C2)cc1] | 3-(1',5-bis(4-methoxyphenyl)-3'-(p-tolyl)-3,4-dihydro-1'H,2H-[3,4'-bipyrazole]-2-carbonyl)benzoic acid |
| 11 | 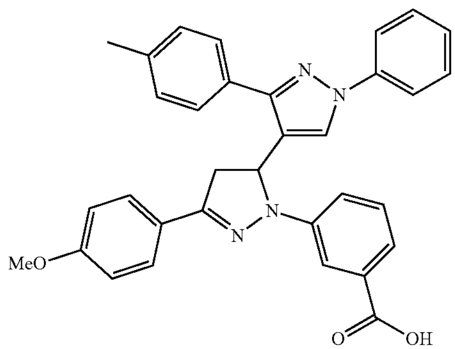 [SMILES: COc1ccc(C2=NN(c3cccc(C(=O)O)c3)C(c3cn(-c4ccccc4)nc3-c3ccc(C)cc3)C2)cc1] | 3-(5-(4-methoxyphenyl)-1'-phenyl-3'-(p-tolyl)-3,4-dihydro-1'H,2H-[3,4'-bipyrazol]-2-yl)benzoic acid |
| 12 | 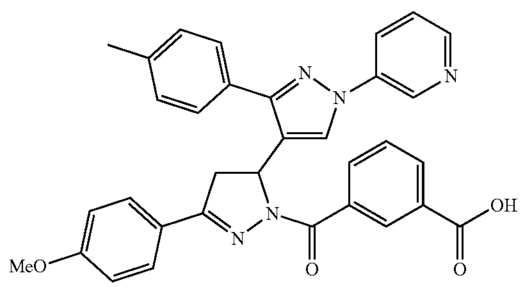 [SMILES: COc1ccc(C2=NN(C(=O)c3cccc(C(=O)O)c3)C(c3cn(-c4cccnc4)nc3-c3ccc(C)cc3)C2)cc1] | 3-(5-(4-methoxyphenyl)-1'-(pyridin-3-yl)-3'-(p-tolyl)-3,4-dihydro-1'H,2H-[3,4'-bipyrazole]-2-carbonyl)benzoic acid |
| 13 | 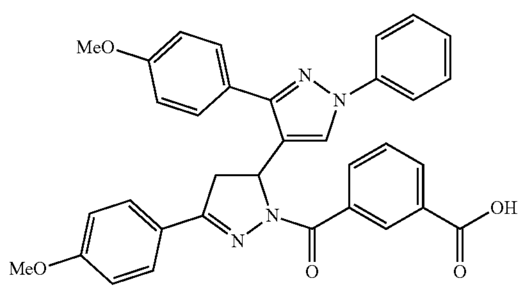 [SMILES: COc1ccc(C2=NN(C(=O)c3cccc(C(=O)O)c3)C(c3cn(-c4ccccc4)nc3-c3ccc(OC)cc3)C2)cc1] | 3-(3',5-bis(4-methoxyphenyl)-1'-phenyl-3,4-dihydro-1'H,2H-[3,4'-bipyrazole]-2-carbonyl)benzoic acid |
| 14 | 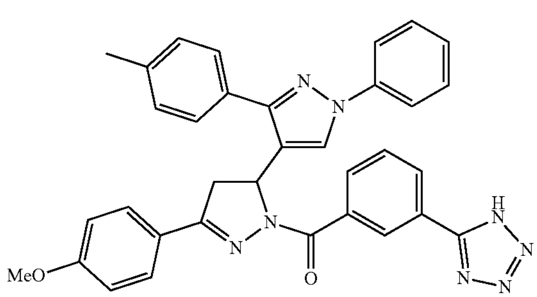 [SMILES: COc1ccc(C2=NN(C(=O)c3cccc(-c4nnn[nH]4)c3)C(c3cn(-c4ccccc4)nc3-c3ccc(C)cc3)C2)cc1] | (3-(1H-tetrazol-5-yl)phenyl)(5-(4-methoxyphenyl)-1'-phenyl-3'-(p-tolyl)-3,4-dihydro-1'H,2H-[3,4'-bipyrazol]-2-yl)methanone |

| Compound | Structure | Name |
|---|---|---|
| 15 | 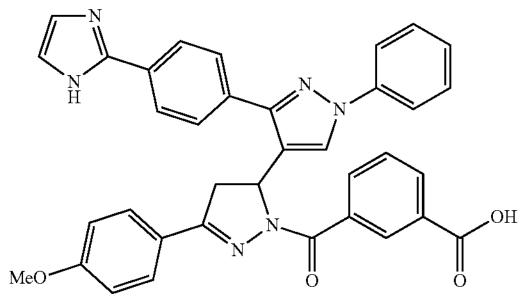 [SMILES: COc1ccc(C2=NN(C(=O)c3cccc(C(=O)O)c3)C(c3cn(-c4ccccc4)nc3-c3ccc(-c4ncc[nH]4)cc3)C2)cc1] | 3-(3'-(4-(1H-imidazol-2-yl)phenyl)-5-(4-methoxyphenyl)-1'-phenyl-3,4-dihydro-1'H,2H-[3,4'-bipyrazole]-2-carbonyl)benzoic acid |

Those skilled in the art will recognize that the species listed or illustrated herein are not exhaustive, and that additional species within the scope of these defined terms may be selected.

Pharmaceutical Compositions

For treatment purposes, pharmaceutical compositions comprising the compounds described herein may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the invention are sterile compositions. Pharmaceutical compositions may be prepared using compounding techniques known or that become available to those skilled in the art.

Sterile compositions are also contemplated by the invention, including compositions that are in accord with national and local regulations governing such compositions.

The pharmaceutical compositions and compounds described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the invention may be administered by a suitable route of delivery, such as oral, parenteral, rectal, nasal, topical, or ocular routes, or by inhalation. Preferably, the compositions are formulated for intravenous or oral administration.

For oral administration, the compounds the invention may be provided in a solid form, such as a tablet or capsule, or as a solution, emulsion, or suspension. To prepare the oral compositions, the compounds of the invention may be formulated to yield a dosage of, e.g., from about 0.1 mg to 1 g daily, or about 1 mg to 50 mg daily, or about 50 to 250 mg daily, or about 250 mg to 1 g daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier. The inventive compositions may be formulated for rectal administration as a suppository.

For topical applications, the compounds of the present invention are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the invention may utilize a patch formulation to effect transdermal delivery.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The term "subject" refers to a mammalian patient in need of such treatment, such as a human.

A compound of Formula (1) or Formula (1a) may be used in a method to treat a neurological disorder in a patient in need of such treatment. Illustratively, the method may comprise administering to the patient an effective amount of a compound of Formula 1 or Formula (1a) or a pharmaceutically acceptable salt thereof.

A compound of Formula (1), or Formula (1a), or a pharmaceutically acceptable salt thereof, may also be used for the manufacture of a medicament for the treatment of pain.

In some embodiments, a compound of Formula (1) or Formula (1a) or a pharmaceutically acceptable salt thereof may be used in a method to treat a neurological disorder such as pain in a mammal in need thereof. The method comprises administering to the mammal in need of treatment an effective amount of a compound, or a pharmaceutically acceptable salt thereof of Formula (1) or Formula (1a). In some embodiments, neurological disorders that may be treated with compounds of Formula (1) or Formula (1a) include, but are not limited to, pain, chronic pain, diabetic neuropathy, neuropathy secondary to nerve trauma, trigeminal neuralgia, post herpetic neuralgia, cancer pain and AIDS-related neuropathy.

In some embodiments, a method to modulate protein-protein interaction between pore and auxiliary subunits of a voltage-gated ion channel in a nerve cell, comprises contacting the nerve cell with an effective amount of the compound of Formula (1) or Formula (1a) or a pharmaceutically acceptable salt thereof. In one embodiment, the pore forming subunit is CaVα1. In another embodiment, the auxiliary subunit is CaVβ. In another embodiment, the auxiliary subunit is CaVβ3.

In illustrative embodiments, the compounds of Formula (1) or Formula (1a) are generally effective over a wide dosage range. For example, dosages per day normally fall within the range of about 0.1 mg/kg to about 1.0 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present disclosure can be described as embodiments in any of the following enumerated clauses. It will be understood that any of the embodiments described herein can be used in connection with any other embodiments described herein to the extent that the embodiments do not contradict one another.

Clause 1. A compound of Formula (1a)

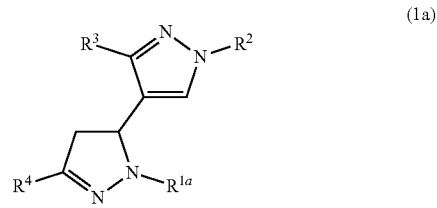

wherein $R^{1a}$ is C(O)$R^1$ or phenyl optionally substituted with one or more —CO$_2$H, —C(O)OC$_1$-C$_4$ alkyl, or heteroaryl, wherein $R^1$ is —C$_1$-C$_4$ alkyl-CO$_2$H, —C$_1$-C$_4$ alkyl-C(O)C$_1$-C$_4$ alkyl, or phenyl, wherein each hydrogen atom in phenyl is independently optionally substituted with —CO$_2$H, —C(O)OC$_1$-C$_4$ alkyl, or heteroaryl;

$R^2$ is phenyl, heteroaryl, —C$_1$-C$_4$ alkyl-phenyl, or —C$_1$-C$_4$ alkyl, wherein each hydrogen atom in phenyl is independently optionally substituted with —C$_1$-C$_4$ alkoxy;

$R^3$ is phenyl, wherein each hydrogen atom in phenyl is independently optionally substituted with —C$_1$-C$_3$ alkyl, halo, —C$_1$-C$_4$ alkoxy, or heteroaryl; and $R^4$ is phenyl, wherein each hydrogen atom in phenyl is independently optionally substituted with —C$_1$-C$_4$ alkoxy, piperazinyl, or heteroaryl;

with the proviso that the compound of Formula (1a) is not

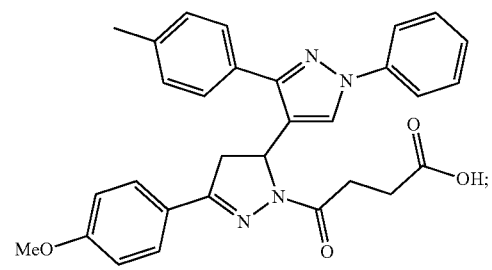

or a pharmaceutically acceptable salt thereof.

Clause 2. A compound of Formula (1)

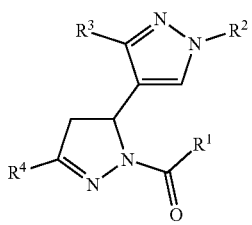

wherein
$R^1$ is selected from the group consisting of $(C_1$-$C_4$ alkyl)-$CO_2H$, and —$CO_2H$ and tetrazole substituted phenyl;
$R^2$ is selected from the group consisting of phenyl, methoxy substituted phenyl, and pyridinyl;
$R^3$ is selected from the group consisting of $(C_1$-$C_3$ alkyl) substituted phenyl and halo substituted phenyl; and
$R^4$ is selected from the group consisting of alkoxy substituted phenyl and phenyl substituted pyridyl;
with the proviso that the compound of Formula (1) is not

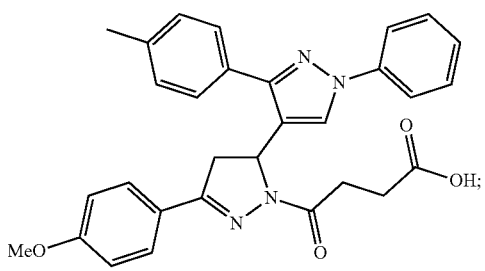

or a pharmaceutically acceptable salt thereof.

Clause 3. The compound or pharmaceutically acceptable salt thereof of any of the preceding clauses, wherein $R^1$ is selected from the group consisting of —$CO_2H$ substituted phenyl, tetrazole substituted phenyl, and —$(CH_2)_2CO_2H$.

Clause 4. The compound or pharmaceutically acceptable salt thereof of any of the preceding clauses, wherein $R^1$ is —$(CH_2)_2CO_2H$.

Clause 5. The compound or pharmaceutically acceptable salt thereof of any of the preceding clauses, wherein $R^2$ is phenyl, methoxy substituted phenyl, or heteroaryl.

Clause 6. The compound or pharmaceutically acceptable salt thereof of any of the preceding clauses, wherein $R^2$ is phenyl.

Clause 7. The compound or pharmaceutically acceptable salt thereof of any of the preceding clauses, wherein $R^2$ is methoxy substituted phenyl.

Clause 8. The compound or pharmaceutically acceptable salt thereof of any of the preceding clauses, wherein $R^3$ is methyl-phenyl or chloro-phenyl.

Clause 9. The compound or pharmaceutically acceptable salt thereof of any of the preceding clauses, wherein $R^4$ is methoxy-phenyl or phenyl pyridyl.

Clause 10. The compound or pharmaceutically acceptable salt thereof of any of the preceding clauses that is selected from the group consisting of 4-(1'-isopropyl-5-(4-methoxyphenyl)-3'-(p-tolyl)-1H,1'H-[3,4'-bipyrazol]-2(5H)-yl)-4-oxobutanoic acid, 3-(3'-(4-chlorophenyl)-5-(4-methoxyphenyl)-1'-phenyl-3,4-dihydro-1'H,2H-[3,4'-bipyrazole]-2-carbonyl)benzoic acid, 3-(1',5-bis(4-methoxyphenyl)-3'-(p-tolyl)-3,4-dihydro-1'H,2H-[3,4'-bipyrazole]-2-carbonyl) benzoic acid, and 3-(3'-(4-methylphenyl)-5-(4-methoxyphenyl)-1'-phenyl-3,4-dihydro-1'H,2H-[3,4'-bipyrazole]-2-tetrazole.

Clause 11. A pharmaceutical composition comprising a compound according to any of the preceding clauses, or a pharmaceutically acceptable salt thereof, and at least one of a pharmaceutically acceptable carrier, diluent or excipient.

Clause 12. A method to treat a neurological disorder in a mammal in need thereof, comprising administering an effective amount of a compound, or a pharmaceutically acceptable salt thereof of a compound of Formula (1a)

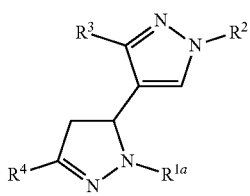

wherein
$R^{1a}$ is $C(O)R^1$ or phenyl optionally substituted with one or more —$CO_2H$, —$C(O)OC_1$-$C_4$ alkyl, or heteroaryl, wherein $R^1$ is —$C_1$-$C_4$ alkyl-$CO_2H$, —$C_1$-$C_4$ alkyl-C(O)$C_1$-$C_4$ alkyl, or phenyl, wherein each hydrogen atom in phenyl is independently optionally substituted with —$CO_2H$, —$C(O)OC_1$-$C_4$ alkyl, or heteroaryl;
$R^2$ is phenyl, heteroaryl, —$C_1$-$C_4$ alkyl-phenyl, or —$C_1$-$C_4$ alkyl, wherein each hydrogen atom in phenyl is independently optionally substituted with —$C_1$-$C_4$ alkoxy;
$R^3$ is phenyl, wherein each hydrogen atom in phenyl is independently optionally substituted with —$C_1$-$C_3$ alkyl, halo, —$C_1$-$C_4$ alkoxy, or heteroaryl; and
$R^4$ is phenyl, wherein each hydrogen atom in phenyl is independently optionally substituted with —$C_1$-$C_4$ alkoxy, piperazinyl, or heteroaryl;
or a pharmaceutically acceptable salt thereof.

Clause 13. A method to treat a neurological disorder in a mammal in need thereof, comprising administering an effective amount of a compound, or a pharmaceutically acceptable salt thereof of a compound of of Formula (1)

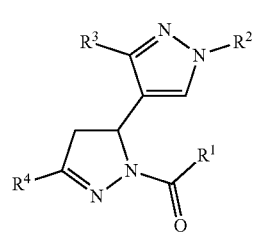

wherein
$R^1$ is selected from the group consisting of —$(C_1$-$C_4$ alkyl)-$CO_2H$, and —$CO_2H$ and tetrazole substituted phenyl;
$R^2$ is selected from the group consisting of phenyl, methoxy substituted phenyl, and pyridinyl;
$R^3$ is selected from the group consisting of $(C_1$-$C_3$ alkyl) substituted phenyl and halo substituted phenyl; and R⁴ is selected from the group consisting of alkoxy substituted phenyl and phenyl substituted pyridyl.

Clause 14. The method of clause 12 or clause 13, wherein the neurological disorder is pain.

Clause 15. The method of any of clauses 12-14, wherein $R^1$ is selected from the group consisting of CO₂H substituted phenyl, tetrazole substituted phenyl, and —(CH₂)₂CO₂H.

Clause 16. The method of any of clauses 12-15, wherein $R^1$ is —(CH₂)₂CO₂H.

Clause 17. The method of any of clauses 12-16, wherein $R^2$ is phenyl, methoxy substituted phenyl, or heteroaryl.

Clause 18. The method of any of clauses 12-17, wherein $R^2$ is phenyl.

Clause 19. The method of any of clauses 12-18, wherein $R^2$ is methoxy substituted phenyl.

Clause 20. The method of any of clauses 12-19, wherein $R^3$ is methyl-phenyl or chloro-phenyl.

Clause 21. The method of any of clauses 12-20, wherein $R^4$ is methoxy-phenyl or phenyl substituted with pyridyl.

Clause 22. The method of any of clauses 12-21, wherein the compound is selected from the group consisting of 4-(1'-isopropyl-5-(4-methoxyphenyl)-3'-(p-tolyl)-1H,1'H-[3,4'-bipyrazol]-2(5H)-yl)-4-oxobutanoic acid, 3-(3'-(4-chlorophenyl)-5-(4-methoxyphenyl)-1'-phenyl-3,4-dihydro-1'H,2H-[3,4'-bipyrazole]-2-carbonyl)benzoic acid, 3-(1',5-bis(4-methoxyphenyl)-3'-(p-tolyl)-3,4-dihydro-1'H,2H-[3,4'-bipyrazole]-2-carbonyl)benzoic acid, and 3-(3'-(4-methylphenyl)-5-(4-methoxyphenyl)-1'-phenyl-3,4-dihydro-1'H,2H-[3,4'-bipyrazole]-2-tetrazole.

Clause 23. A method to modulate a protein-protein interaction between pore and auxiliary subunits of a voltage-gated ion channel in a nerve cell, comprising contacting the nerve cell with an effective amount of the compound of Formula (1a)

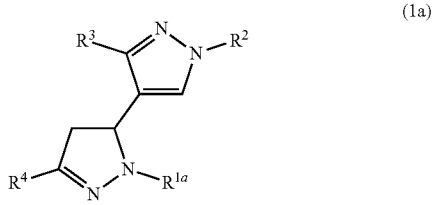

(1a)

wherein $R^{1a}$ is C(O)R¹ or phenyl optionally substituted with one or more —CO₂H, —C(O)OC₁-C₄ alkyl, or heteroaryl, wherein R¹ is —C₁-C₄ alkyl-CO₂H, —C₁-C₄ alkyl-C(O)C₁-C₄ alkyl, or phenyl, wherein each hydrogen atom in phenyl is independently optionally substituted with —CO₂H, —C(O)OC₁-C₄ alkyl, or heteroaryl;

$R^2$ is phenyl, heteroaryl, —C₁-C₄ alkyl-phenyl, or —C₁-C₄ alkyl, wherein each hydrogen atom in phenyl is independently optionally substituted with —C₁-C₄ alkoxy;

$R^3$ is phenyl, wherein each hydrogen atom in phenyl is independently optionally substituted with —C₁-C₃ alkyl, halo, —C₁-C₄ alkoxy, or heteroaryl; and $R^4$ is phenyl, wherein each hydrogen atom in phenyl is independently optionally substituted with —C₁-C₄ alkoxy, piperazinyl, or heteroaryl;

or a pharmaceutically acceptable salt thereof.

Clause 24. A method to modulate a protein-protein interaction between pore and auxiliary subunits of a voltage-gated ion channel in a nerve cell, comprising contacting the nerve cell with an effective amount of the compound of Formula (1)

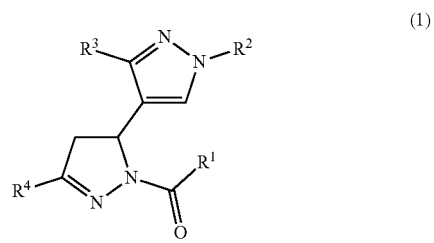

(1)

wherein $R^1$ is selected from the group consisting of —(C₁-C₄ alkyl)-CO₂H, and —CO₂H and tetrazole substituted phenyl;

$R^2$ is selected from the group consisting of phenyl, methoxy substituted phenyl, and pyridinyl;

$R^3$ is selected from the group consisting of (C₁-C₃ alkyl) substituted phenyl and halo substituted phenyl; and $R^4$ is selected from the group consisting of alkoxy substituted phenyl and phenyl substituted pyridyl.

Clause 25. The method of clause 23 or clause 24, wherein the pore forming subunit is CaVα1.

Clause 26. The method of any of clauses 23-25, wherein the the auxiliary subunit is CaVβ or a pharmaceutically acceptable salt thereof.

Clause 27. The method of any of clauses 23-26, wherein the neurological disorder is pain.

Clause 28. The method of any of clauses 23-27, wherein $R^1$ is selected from the group consisting of CO₂H substituted phenyl, tetrazole substituted phenyl, and —(CH₂)₂CO₂H.

Clause 29. The method of any of clauses 23-28, wherein $R^1$ is —(CH₂)₂CO₂H.

Clause 30. The method of any of clauses 23-29, wherein $R^2$ is phenyl, methoxy substituted phenyl, or heteroaryl.

Clause 31. The method of any of clauses 23-30, wherein $R^2$ is phenyl.

Clause 32. The method of any of clauses 23-31, wherein $R^2$ is methoxy substituted phenyl.

Clause 33. The method of any of clauses 23-32, wherein $R^3$ is methyl-phenyl or chloro-phenyl.

Clause 34. The method of any of clauses 23-33, wherein $R^4$ is methoxy-phenyl or phenyl substituted with pyridyl.

Clause 35. The method of any of clauses 23-34, wherein the compound is selected from the group consisting of 4-(1'-isopropyl-5-(4-methoxyphenyl)-3'-(p-tolyl)-1H,1'H-[3,4'-bipyrazol]-2(5H)-yl)-4-oxobutanoic acid, 3-(3'-(4-chlorophenyl)-5-(4-methoxyphenyl)-1'-phenyl-3,4-dihydro-1'H,2H-[3,4'-bipyrazole]-2-carbonyl)benzoic acid, 3-(1',5-bis(4-methoxyphenyl)-3'-(p-tolyl)-3,4-dihydro-1'H,2H-[3,4'-bipyrazole]-2-carbonyl)benzoic acid, and 3-(3'-(4-methylphenyl)-5-(4-methoxyphenyl)-1'-phenyl-3,4-dihydro-1'H,2H-[3,4'-bipyrazole]-2-tetrazole.

Clause 36. A compound selected from the group consisting of
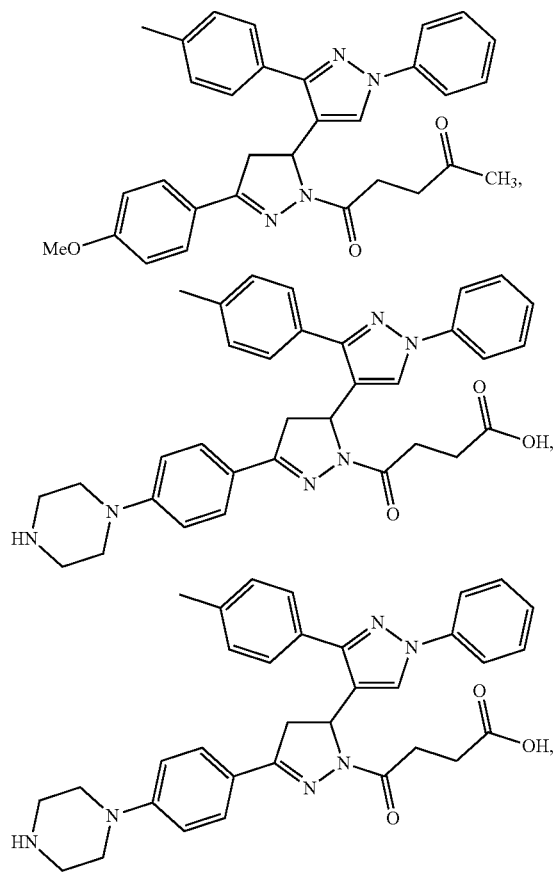
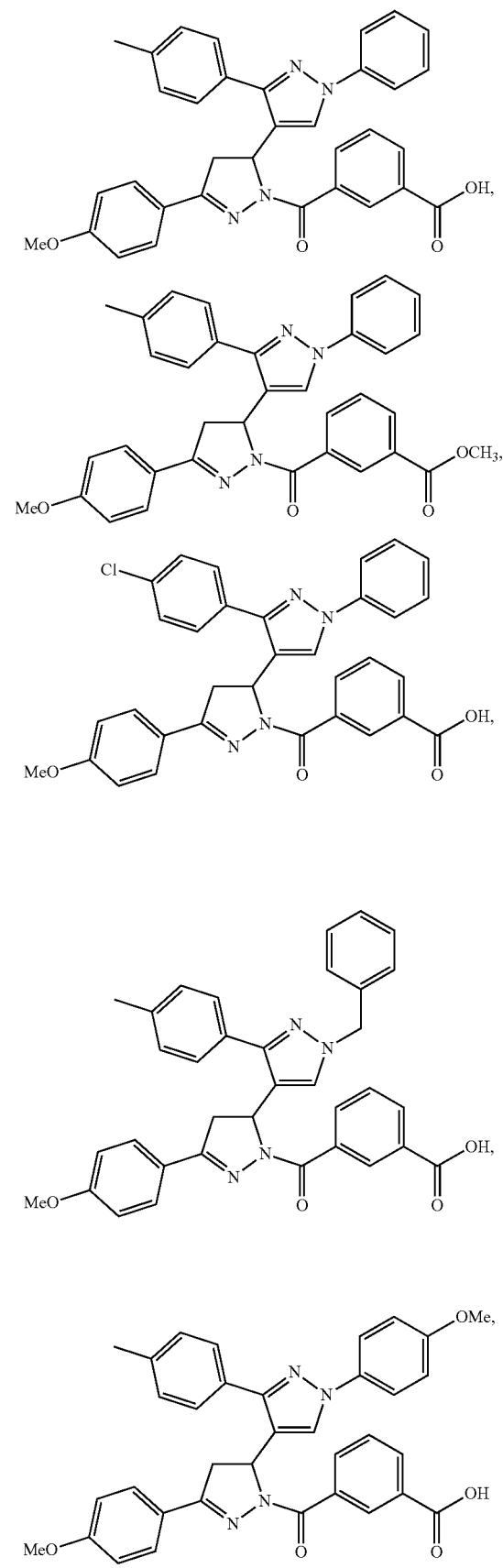

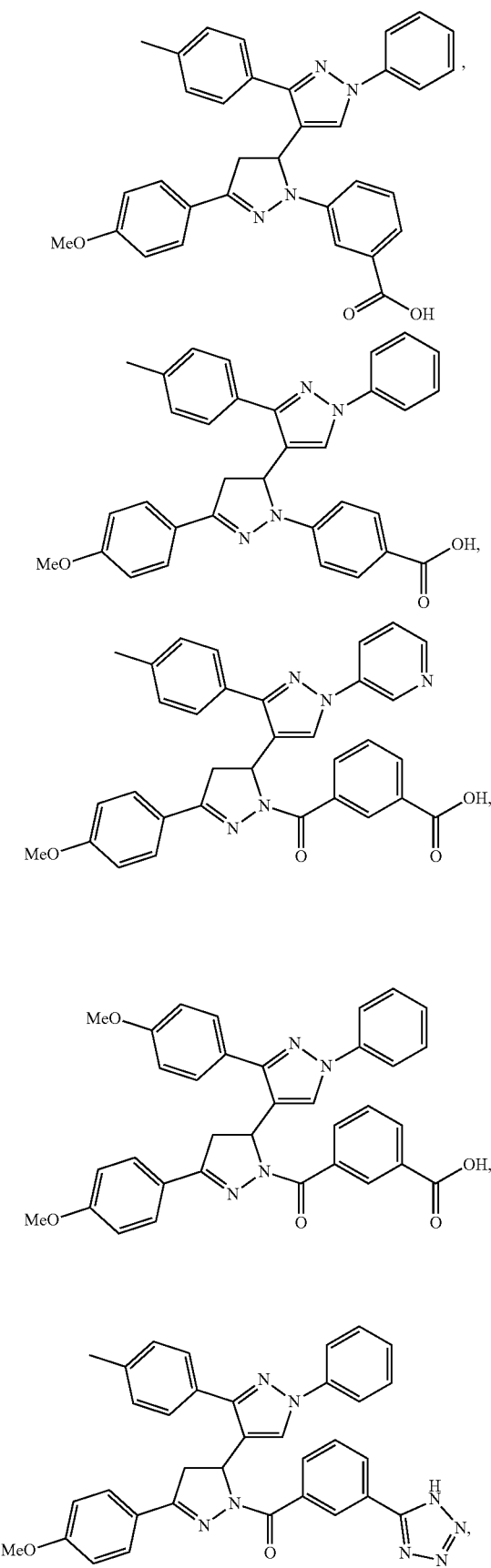
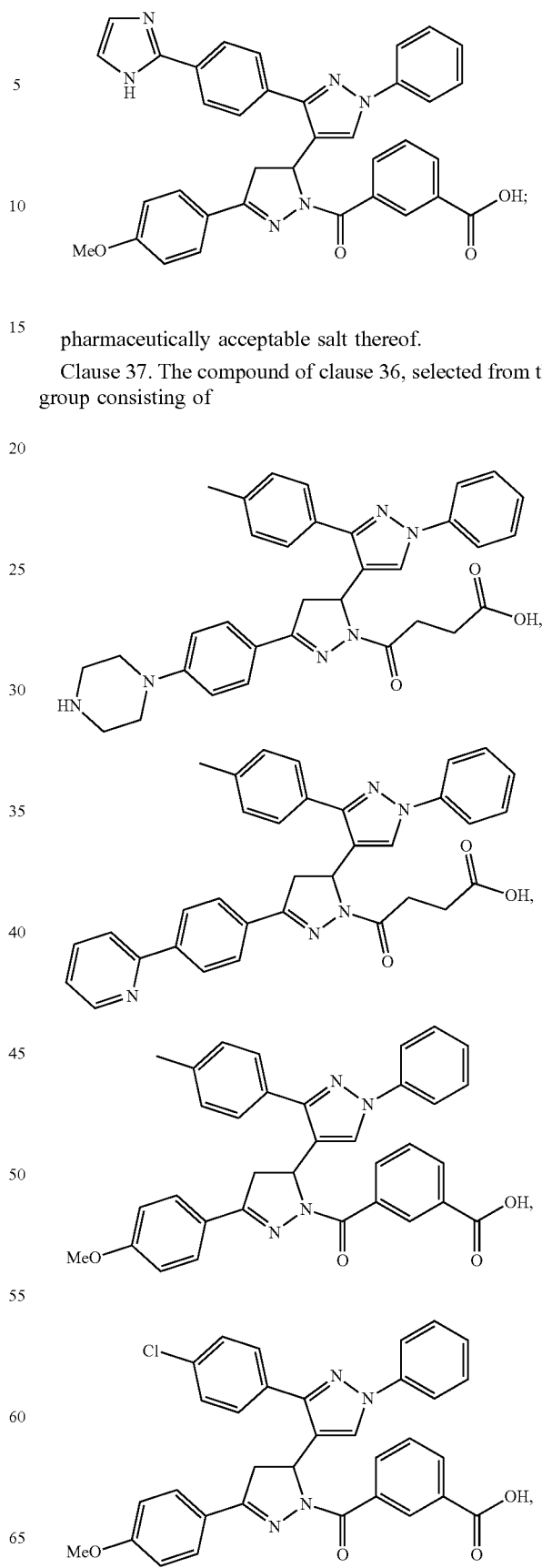
pharmaceutically acceptable salt thereof.
Clause 37. The compound of clause 36, selected from the group consisting of

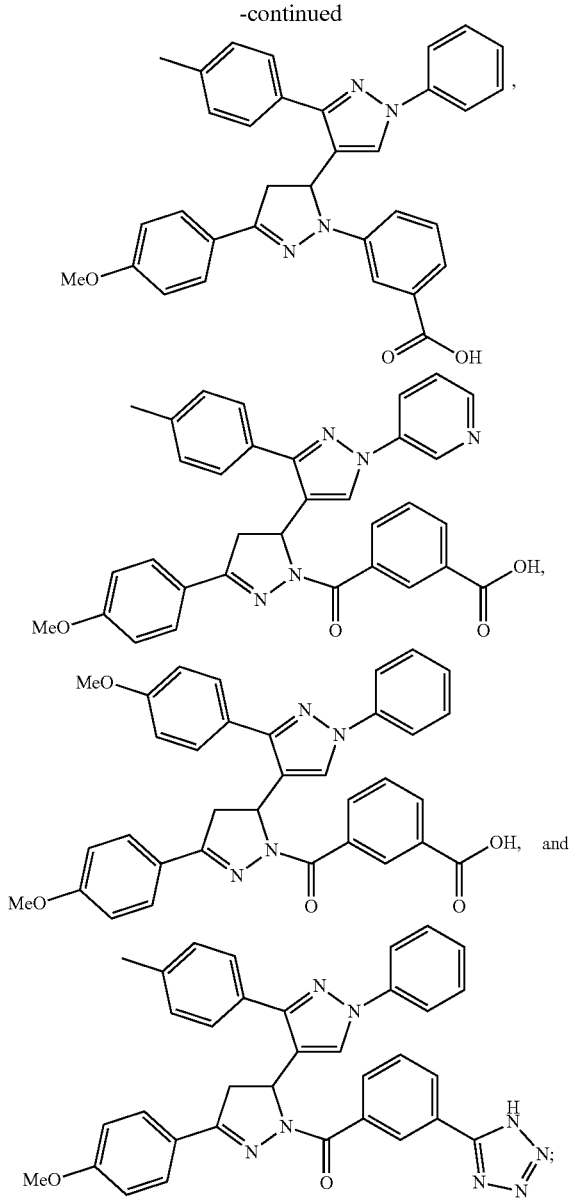

pharmaceutically acceptable salt thereof.

Clause 38. Use of a compound according to any one of clauses 1-10, 36, or 37, or a pharmaceutically acceptable salt thereof, in the manufacture of a medicament for use in treating a neurological disorder in a patient.

Clause 39. The use of clause 38, wherein the neurological disorder is pain.

Clause 40. A compound according to any one of clauses 1-10, 36, or 37, or a pharmaceutically acceptable salt thereof, for treating a neurological disorder in a patient.

Chemical Synthesis

Exemplary chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Abbreviations

The examples described herein use materials, including but not limited to, those described by the following abbreviations known to those skilled in the art:

| | |
|---|---|
| g | grams |
| eq | equivalents |
| mmol | millimoles |
| mL | milliliters |
| EtOAc or EA | ethyl acetate |
| MHz | megahertz |
| Ppm | parts per million |
| S | singlet |
| D | doublet |
| T | triplet |
| Q | quartet |
| Quin | quintet |
| Br | broad |
| M | multiplet |
| dd | doublet of doublets |
| Hz | hertz |
| THF | tetrahydrofuran |
| ° C. | degrees Celsius |
| $R_f$ | retardation factor |
| N | normal |
| J | coupling constant |
| DMSO-$d_6$ | deuterated dimethyl sulfoxide |
| CDCl$_3$ | deuterated chloroform |
| min | minutes |
| h | hours |
| TLC | thin layer chromatography |
| M | molar |
| ESIMS | electrospray ionization mass spectrum |
| m/z | mass-to-charge ratio |
| Ms | methanesulfonyl |
| FDPP | pentafluorophenyl diphenylphosphinate |
| μM | micromolar |
| IC$_{50}$ | half maximal inhibitory concentration |
| DMF | N,N-dimethylformamide |
| Hex | hexanes |
| Ac | acetyl |
| PE | petroleum ether |
| EtOH | ethanol |
| MeOH | methanol |
| xPhos | 2-Dicyclohexylphosphino-2',4',6'-triisopropylbiphenyl |
| atm | atmosphere |

General Method 1

The compounds of the present invention, or salts thereof, may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Others may be made by standard techniques of organic and heterocyclic chemistry which are analogous to the syntheses of known structurally-similar compounds and the procedures described herein which follow including any novel procedures. Without limiting the scope of the invention, the following schemes, preparations, and examples are provided to further illustrate the invention. In addition, one of ordinary skill in the art appreciates that the compounds of Formula 1 may be prepared by using starting material with the corresponding stereochemical configuration which can be prepared by one of skill in the art.

Scheme 1

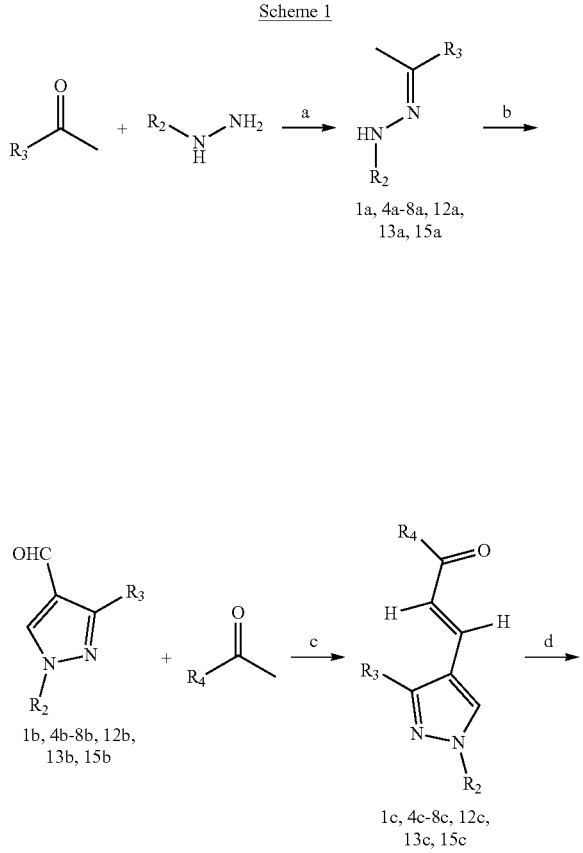
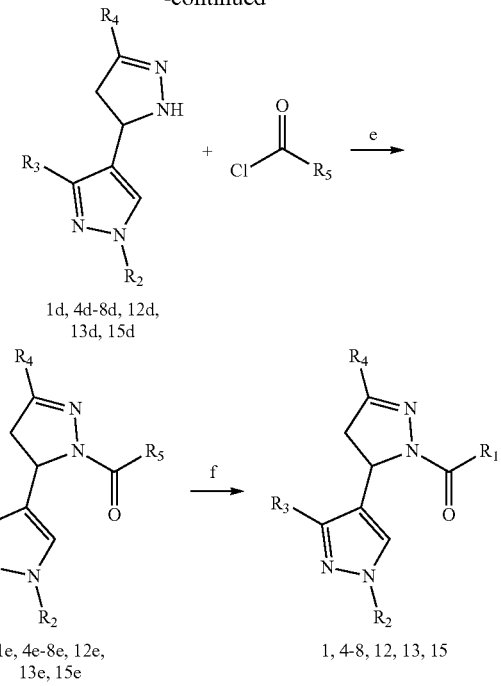

A compound of Formula 1 can be prepared in accordance with reactions as depicted in Scheme 1. With reference to compounds of Formula (1) or Formula (1a), intermediate compound 1a can be synthesized from phenylhydrazine and 4'-methylacetophenone by simple condensation (step a). Intermediate 1a can be stored in darkness, under argon gas at 4° C. Excess Vilsmeier reagent (DMF+POCl₃) can be added to intermediate 1a to generate intermediate 1b (step b). Condensation with substituted acetophenones yields the intermediate enone 1c (step c). Subsequent coupling with excess hydrazine hydride yields the second 4,5-dihydropyrazole ring in intermediate compound 1d (step d). An amidation can be carried out using anhydrous pyridine to generate intermediate 1e (step e). Hydrolysis using 2M LiOH aqueous solution in methanol/THF co-solvents at r.t. results in compound 1(step f).

The following preparations and examples further illustrate the invention and represent typical synthesis of the compounds of Formula (1).

| | | | Compound | | |
|---|---|---|---|---|---|
| Example | $R^1$ | $R^2$ | $R^3$ | $R^4$ | $K_i$ (µM) |
| 1-6 | (CH₂)₂CO₂H | Ph | 4-Me—Ph | 4-MeO—Ph | 6.7 ± 0.3 |
| 2 | (CH₂)₂C(O)CH₃ | Ph | 4-Me—Ph | 4-MeO—Ph | NA |
| 3-12 | (CH₂)₂CO₂H | Ph | 4-Me—Ph | 1-piperazinyl-Ph | NA |
| 4-17 | (CH₂)₂CO₂H | Ph | 4-Me—Ph | 2-pyridinyl-Ph | 2.2 ± 0.3 |
| 5-23 | (CH₂)₂CO₂H | iso-Pr | 4-Me—Ph | 4-MeO—Ph | NA |
| 6-24 | 3-Ph—AcOH | Ph | 4-Me—Ph | 4-MeO—Ph | 1.4 ± 0.1 |
| 7-24 | 3-Ph—C(O)Me | Ph | 4-Me—Ph | 4-MeO—Ph | NA |
| 8-31 | 3-Ph—AcOH | Ph | 4-Cl—Ph | 4-MeO—Ph | 1.2 ± 0.1 |
| 9-37 | 3-Ph—AcOH | Bzl | 4-Me—Ph | 4-MeO—Ph | NA |
| 43-10 | 3-Ph—AcOH | 4-MeO—Ph | 4-Me—Ph | 4-MeO—Ph | 3.7 ± 0.2 |
| 45-11** | 3-Ph—AcOH | Ph | 4-Me—Ph | 4-MeO—Ph | 3.9 ± 0.9 |
| 51-12 | 3-Ph—AcOH | 3-pyridinyl | 4-Me—Ph | 4-MeO—Ph | 5.0 ± 1.9 |
| 57-13 | 3-Ph—AcOH | Ph | 4-MeO—Ph | 4-MeO—Ph | NA |
| 59-14 | 3-Ph-tetrazolyl | Ph | 4-Me—Ph | 4-MeO—Ph | 2.0 ± 0.2 |
| 66-15 | 3-Ph—AcOH | Ph | 2-imidazolyl-Ph | 4-MeO—Ph | NA |

**indicates that the amide bond is missing from this compound.

Example 1-1a 1-phenyl-2-(1-phenylethylidene)-hydrazine

A mixture of 1-(p-tolyl)ethanone (2.68 g, 20 mmol), phenylhydrazine (2.16 g, 20 mmol) and acetic acid (260 mg, 2 mmol) in anhydrous ethanol (25 mL) was refluxed under $N_2$ for 12 h. After removal of ethanol, the residue was dissolved in ethyl acetate (100 mL). The organic phase was washed with water (100 mL), dried over $Na_2SO_4$ and concentrated under reduced pressure. The residue was purified by column chromatography with PE/EA (8:1) to give the desired product as a light yellow solid (3.6 g, 86% yield). $^1$H NMR (400 MHz, CDCl$_3$) δ 7.69 (d, J=8.0 Hz, 2H), 7.30-7.26 (m, 2H), 7.18 (m, 4H), 6.87 (t, J=7.2 Hz, 1H), 2.37 (s, 3H), 2.23 (s, 3H). ESIMS (m/z) for $C_{15}H_{17}N_2^+$ [M+H]$^+$: calculated 225.11, found 225.10.

Example 2-1b 1-phenyl-5-(p-tolyl)-1H-pyrazole-3-carbaldehyde

A solution of 1-phenyl-2-(1-phenylethylidene)hydrazine (1.8 g, 8.6 mmol) in the Vilsmeier reagent (20 mL) was stirred at 65° C. overnight. The mixture was cooled to room temperature, and poured into an ice-water (50 mL). The product (2 g, 89% yield) was obtained upon neutralization with NaHCO$_3$ and filtration. $^1$H NMR (400 MHz, CDCl$_3$): δ 10.05 (s, 1H), 8.53 (s, 1H), 7.80-7.78 (d, J=8.0 Hz, 2H), 7.73-7.71 (d, J=8.0 Hz, 2H), 7.53-7.49 (m, 2H), 7.39 (m, 1H), 7.32-7.31 (d, J=7.6 Hz, 2H), 2.43 (s, 3H). ESIMS (m/z) for $C_{17}H_{15}N_2O^+$ [M+H]$^+$: calculated 263.11, found 263.10.

Example 3-1c 1-(4-methoxyphenyl)-3-(1-phenyl-5-(p-tolyl)-1H-pyrazol-3-yl)prop-2-en-1-one A mixture of 1-phenyl-5-(p-tolyl)-1H-pyrazole-3-carbaldehyde (284 mg, 2.0 mmol) and 1-(4-methoxyphenyl)-ethanone (500 mg, 2.0 mmol) in EtOH (20 mL) was added to a stirred solution of 10% KOH. The reaction mixture was stirred at 25° C. for 3 h. The precipitate was filtered and the solid was washed with EtOH. The solid was collected and dried to give the desired product as a light yellow solid (680 mg, 91% yield). $^1$H NMR (400 MHz, CDCl$_3$): (8.33 (s, 1H), 7.98-7.96 (d, J=8.8 Hz, 2H), 7.90-7.86 (d, J=15.6 Hz, 1H), 7.81-7.79 (d, J=8.4 Hz, 2H), 7.62-7.60 (d, J=8.0 Hz, 2H), 7.53-7.47 (t, J=8.0 Hz, 2H), 7.39-7.26 (m, 4H), 6.97-6.95 (d, J=8.8 Hz, 2H), 3.89 (s, 3H), 2.43 (s, 3H). ESIMS (m/z) for $C_{26}H_{23}N_2O_2^+$ [M+H]$^+$: calculated 395.17, found 395.21.

Example 4-1d

5'-(4-methoxyphenyl)-1-phenyl-5-(p-tolyl)-3',4'-dihydro-1H,2'H-3,3'-bipyrazole

To a solution of 1-(4-methoxyphenyl)-3-(1-phenyl-5-(p-tolyl)-1H-pyrazol-3-yl)-prop-2-en-1-one (400 mg, 1.0 mmol) and hydrazine hydrate (75 mg, 1.5 mmol) in EtOH (20 mL), a few drops of piperidine were added. The reaction of mixture was refluxed for 2.5 h. The suspension was cooled to room temperature, and a white precipitate was filtered and washed with EtOH. The solid was collected and dried to afford the desired product as a white solid (390 mg, 93% yield). 1H NMR (400 MHz, CDCl$_3$): δ 8.02 (s, 1H), 7.73-7.71 (d, J=8.0 Hz, 2H), 7.63-7.60 (m, 4H), 745-7.41 (m, 2H), 7.28 (m, 3H), 6.92-6.90 (d, J=8.8 Hz, 2H), 5.88 (br, 1H), 5.14-5.10 (m, 1H), 3.82 (s, 3H), 3.48-3.42 (m, 1H), 3.08-3.02 (m, 1H), 2.43 (s, 3H). ESIMS (m/z) for $C_{26}H_{25}N_4O^+$ [M+H]$^+$: calculated 409.20, found 409.20.

Example 5-1e 4-(5'-(4-methoxyphenyl)-1-phenyl-5-(p-tolyl)-3',4'-dihydro-1H,2'H-[3,3'-bipyrazol]-2'-yl)-4-oxobutanoate Methyl 4-chloro-4-oxobutanoate (0.24 mmol) was added dropwise to a solution of 5'-(4-methoxyphenyl)-1-phenyl-5-(p-tolyl)-3',4'-dihydro-1H,2'H-3,3'-bipyrazole ((100 mg, 0.24 mmol) in pyridine (3 mL). The mixture was stirred at room temperature overnight. The mixture was evaporated to remove the solvent under reduced pressure, and the residue was dissolved in EA (30 mL). The mixture was washed with water (20 mL×2) and brine (20 mL). The organic phase was dried over Na$_2$SO$_4$, filtered, and concentrated. The residue was purified by column chromatography (PE/EA=3:1) to give the desired product as a white solid (51 mg, 41% yield). $^1$H NMR (400 MHz, CDCl$_3$): δ 7.91 (s, 1H), 7.77-7.75 (d, J=7.6 Hz, 2H), 7.65-7.59 (m, 4H), 7.41-7.37 (m, 2H), 7.26-7.20 (m, 3H), 6.90-6.88 (d, J=8.8 Hz, 2H), 5.93-5.89 (dd, J=11.2, 4.0 Hz, 1H), 3.83 (s, 3H), 3.69 (s, 3H), 3.62-3.55 (dd, J=17.2, 11.2 Hz, 1H), 3.60-3.53 (m, 1H), 3.08-3.02 (m, 1H), 2.96-2.85 (m, 1H), 2.72 (m, 1H), 2.38 (s, 3H). ESIMS (m/z) for $C_{31}H_{31}N_4O_4^+$ [M+H]$^+$: calculated 523.23, found 523.20.

Example 6-1

4-(5'-(4-methoxyphenyl)-1-phenyl-5-(p-tolyl)-3',4'-dihydro-1H,2'H-[3,3'-bipyrazol]-2'-yl)-4-oxobutanoic acid Methyl 4-(5'-(4-methoxyphenyl)-1-phenyl-5-(p-tolyl)-3',4'-dihydro-1H,2'H-[3,3'-bipyrazol]-2'-yl)-4-oxobutanoate (51 mg, 0.1 mmol) was added to a suspension of LiOH·H$_2$O (42 mg, 1.0 mmol) in mixture of THF/MeOH/H$_2$O (5 mL, v/v/v=3:1:1). The mixture was stirred at 25° C. overnight. The mixture was cooled with an ice-bath, and adjusted to pH=4-5 with 1 N HCl The mixture was extracted with EA (15 mL×3). The combine organic layers were washed with water, brine, and dried with Na$_2$SO$_4$. The solution was filtered and concentrated under reduced pressure. The residue was purified by prep. HPLC to afford the desired product as white solid (30.1 mg, 59% yield). $^1$H NMR (400 MHz, CDCl$_3$): δ 7.80 (s, 1H), 7.70-7.68 (d, J=7.6 Hz, 2H), 7.60-7.58 (M, 4H), 7.41-7.37 (m, 2H), 7.26-7.22 (m, 3H), 6.90-6.88 (d, J=8.8 Hz, 2H), 5.90-5.86 (dd, J=11.2, 4.0 Hz, 1H), 3.84 (s, 3H), 3.63-3.56 (dd, J=17.2, 11.2 Hz, 1H), 3.27-3.24 (m, 1H), 3.08-3.00 (m, 2H), 2.81-2.73 (m, 2H), 2.37 (s, 3H); $^{13}$C NMR (100 MHz, CDCl$_3$): δ 161.60, 150.16, 139.88, 137.91, 130.24, 129.32, 129.26, 128.40, 128.15, 126.30, 125.80, 123.66, 121.92, 119.02, 114.12, 55.40, 52.69, 42.09, 29.04, 21.26. ESIMS (m/z) for $C_3H_{29}N_4O_4^+$ [M+H]$^+$: calculated 509.21, found 509.20.

Scheme 2

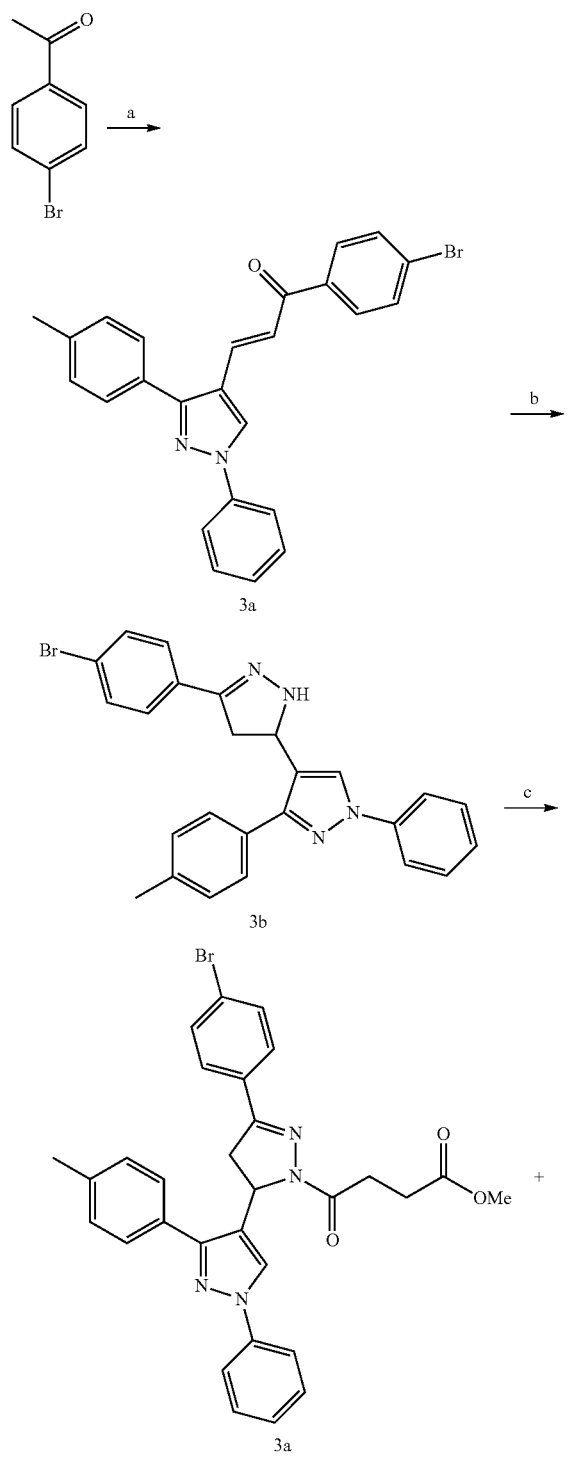

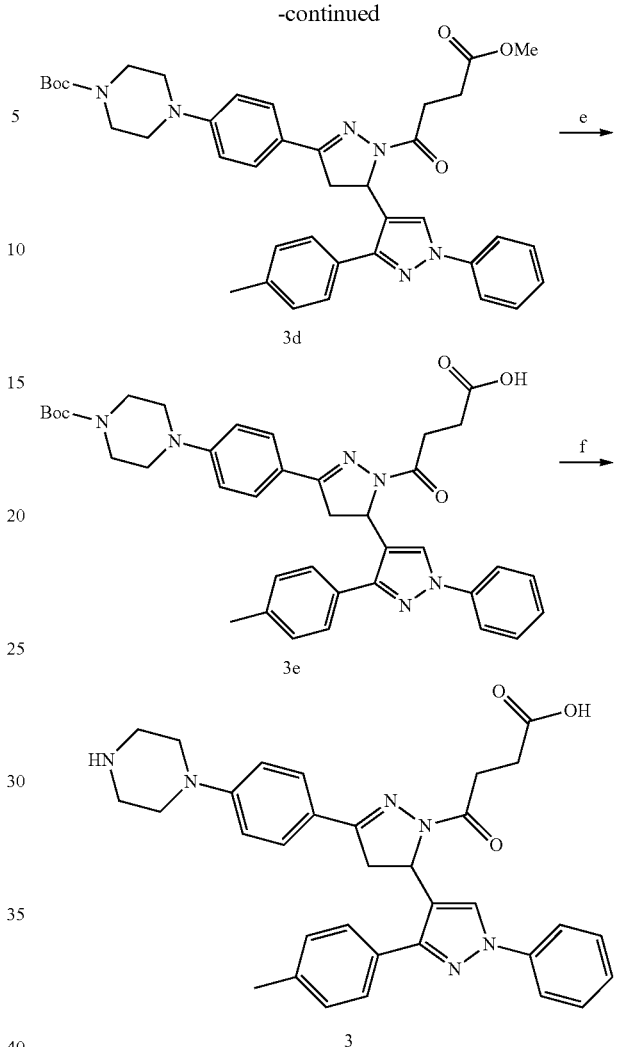

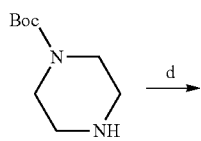

Scheme 2 depicts a route for synthesizing compound 3.

Example 7-3a 1-(4-bromophenyl)-3-(1-phenyl-3-(p-tolyl)-1H-pyrazol-4-yl)prop-2-en-1-one This compound was prepared essentially by the method of Example 3 (1.06 g, 76% yield). $^1$H NMR (400 MHz, CDCl$_3$): δ 8.34 (s, 1H), 7.92-7.88 (d, J=15.6 Hz, 1H), 7.83-7.78 (m, 4H), 7.63-7.58 (m, 4H), 7.52-7.48 (t, J=8.0 Hz, 2H), 7.37-7.26 (m, 4H), 2.43 (s, 3H). ESIMS (m/z) for C$_{25}$H$_{20}$BrN$_2$O$^+$ [M+H]$^+$: calculated 443.07, found 443.10.

Example 8-3b 5-(4-bromophenyl)-1'-phenyl-3'-(p-tolyl)-3,4-dihydro-1'H,2H-3,4'-bipyrazole This compound was prepared essentially by the method of Example 4 (0.49 g, 95% yield). $^1$H NMR (400 MHz, CDCl$_3$): δ 8.00 (s, 1H), 7.71 (d, J=8.0 Hz, 2H), 7.60-7.58 (d, J=8.4 Hz, 2H), 7.45-7.41 (t, J=8.0 Hz, 2H), 7.28-7.26 (m, 3H), 6.01 (br, 1H), 5.18-5.13 (m, 1H), 3.47-3.40 (m, 1H), 3.06-3.00 (m, 1H), 2.41 (s, 3H). ESIMS (m/z) for $C_{25}H_{22}BrN_4^+$ [M+H]$^+$: calculated 457.09, found 457.10.

Example 9-3c

Methyl 4-(5-(4-bromophenyl)-1'-phenyl-3'-(p-tolyl)-3,4-dihydro-1'H,2H-[3,4'-bipyrazol]-2-yl)-4-oxobutanoate This compound was prepared essentially by the method of Example 5 (0.49 g, 95% yield). $^1$H NMR (400 MHz, CDCl$_3$): δ 7.93 (s, 1H), 7.76 (d, J=8.0 Hz, 2H), 7.61 (d, J=8.0 Hz, 2H), 7.60 (m, 4H), 7.41-7.37 (t, J=7.6 Hz, 2H), 7.26-7.21 (m, 4H), 5.92-5.88 (m, 1H), 3.69 (s, 3H), 3.63-3.55 (m, 1H), 3.35 (m, 1H), 3.08-3.02 (m, 1H), 2.93-2.85 (m, 2H), 2.72-2.71 (m, 1H), 2.37 (s, 3H). ESIMS (m/z) for $C_{30}H_{28}BrN_4O_3^+$ [M+H]$^+$: calculated 571.13, found 571.10.

Example 10-3d tert-butyl 4-(4-(2-(4-methoxy-4-oxobutanoyl)-1'-phenyl-3'-(p-tolyl)-3,4-dihydro-1'H,2H-[3,4'-bipyrazol]-5-yl)phenyl)piperazine-1-carboxylate A mixture of intermediate compound 3c (0.1 g, 0.18 mmol), tertbutyl piperazine-1-carboxylate (60 mg, 0.35 mmol), Pd$_2$(dba)$_3$ (32 mg, 0.04 mmol), xPhos (25 mg, 0.05 mmol), and Cs$_2$CO$_3$ (114 mg, 0.35 mmol) in anhydrous dioxane (15 mL) under N$_2$ was refluxed overnight. The solvent was removed. EtOAc (20 mL) was added. The mixture was washed with water and brine. The organic phase was dried with Na$_2$SO$_4$, filtered, and concentrated. The residue was purified by prep.-TLC (PE/AE=2:1) to give the desired product (0.75 g, 49% yield). $^1$H NMR (400 MHz, CDCl$_3$): δ 7.90 (s, 1H), 7.76 (d, J=8.0 Hz, 2H), 7.65 (d, J=7.6 Hz, 2H), 7.56 (d, J=8.0 Hz, 2H), 7.38 (t, J=7.6 Hz, 2H), 7.26-7.21 (m, 4H), 6.85 (d, J=8.4 Hz, 2H), 5.92-5.88 (m, 1H), 3.68 (s, 3H), 3.60-3.54 (m, 5H), 3.40-3.36 (m, 1H), 3.21 (s, 4H), 3.06-3.01 (m, 1H), 2.95-2.85 (m, 2H), 2.72-2.70 (m, 1H), 2.39 (s, 3H), 1.48 (s, 9H). ESIMS (m/z) for $C_{39}H_{45}N_6O_5^+$ [M+H]$^+$: calculated 677.34, found 677.30.

Example 11-3e 4-(5-(4-(4-(tert-butoxycarbonyl)piperazin-1-yl)phenyl)-1'-phenyl-3'-(p-tolyl)-3,4-dihydro-1'H,2H-[3,4'-bipyrazol]-2-yl)-4-oxobutanoic acid This compound was prepared essentially by the method of Example 6 (145 mg, 81% yield). $^1$H NMR (400 MHz, CDCl$_3$): δ 7.79 (s, 1H), 7.70-7.68 (d, J=8.0 Hz, 2H), 7.64-7.62 (d, J=8.0 Hz, 2H), 7.57-7.55 (d, J=8.8 Hz, 2H), 7.42-7.38 (t, J=8.0 Hz, 2H), 7.26-7.23 (m, 4H), 6.87-6.85 (d, J=8.8 Hz, 2H), 5.92-5.88 (dd, J=11.2, 3.6 Hz, 1H), 3.63-3.57 (m, 5H), 3.29-2.24 (m, 5H), 3.11-3.06 (m, 2H), 2.81-2.75 (m, 2H), 2.38 (s, 3H). ESIMS (m/z) for $C_{38}H_{43}N_6O_5^+$ [M+H]$^+$: calculated 663.32, found 663.30.

Example 12-3

4-oxo-4-(1'-phenyl-5-(4-(piperazin-1-yl)phenyl)-3'-(p-tolyl)-3,4-dihydro-1'H,2H-[3,4'-bipyrazol]-2-yl)butanoic acid 4-oxo-4-(1'-phenyl-5-(4-(piperazin-1-yl)phenyl)-3'-(p-tolyl)-3,4-dihydro-1'H,2H-[3,4'-bipyrazol]-2-yl)butanoic acid A solution of intermediate 3e (138 mg, 0.21 mmol) in DCM (0.5 mL) was added to a solution of HCl/DCM (10 mL), and the reaction mixture was stirred at room temperature for 1 h. The solvent was removed. The residue was purified by prep. HPLC to give the desired product as white solid (10 mg, 9% yield). $^1$H NMR (400 MHz, DMSO-d6): δ 8.18 (m, 2H), 7.85 (m, 2H), 7.68 (m, 2H), 7.60 (m, 2H), 7.47 (m, 2H), 7.29 (m, 2H), 6.97 (m, 2H), 5.68 (m, 1H), 3.89-3.77 (m, 10H), 2.95 (m, 4H), 2.37 (s, 3H). ESIMS (m/z) for $C_{33}H_{35}N_6O_3^+$ [M+H]$^+$: calculated 563.27, found 563.30.

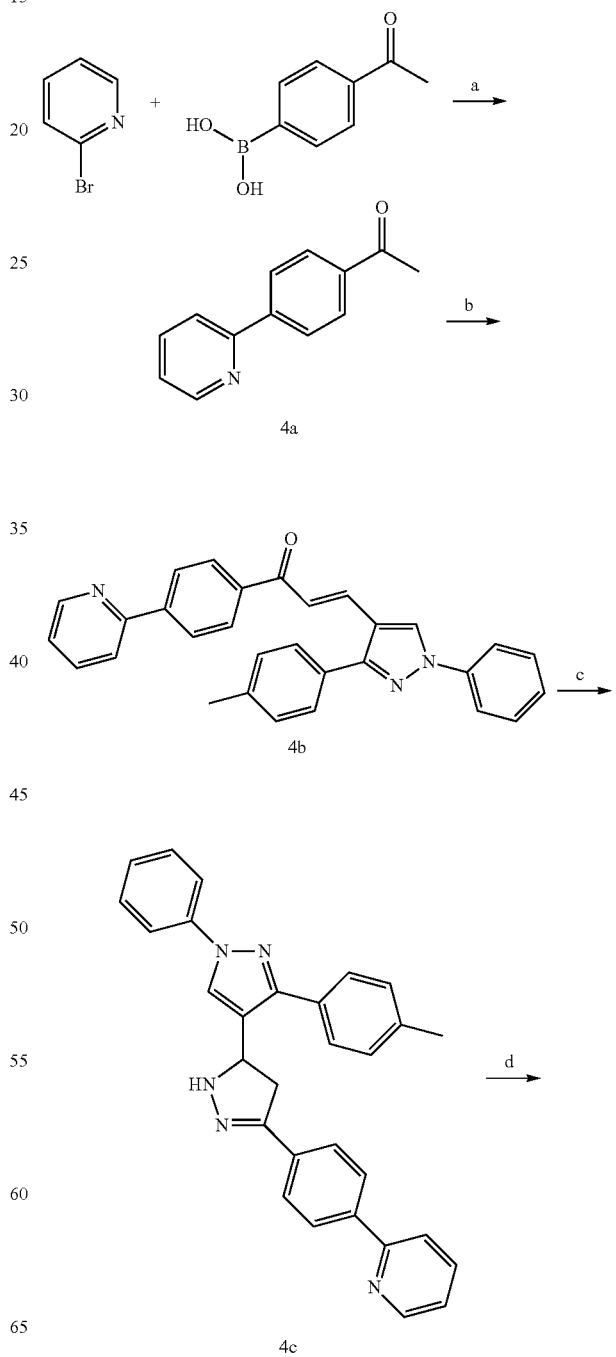

Scheme 3

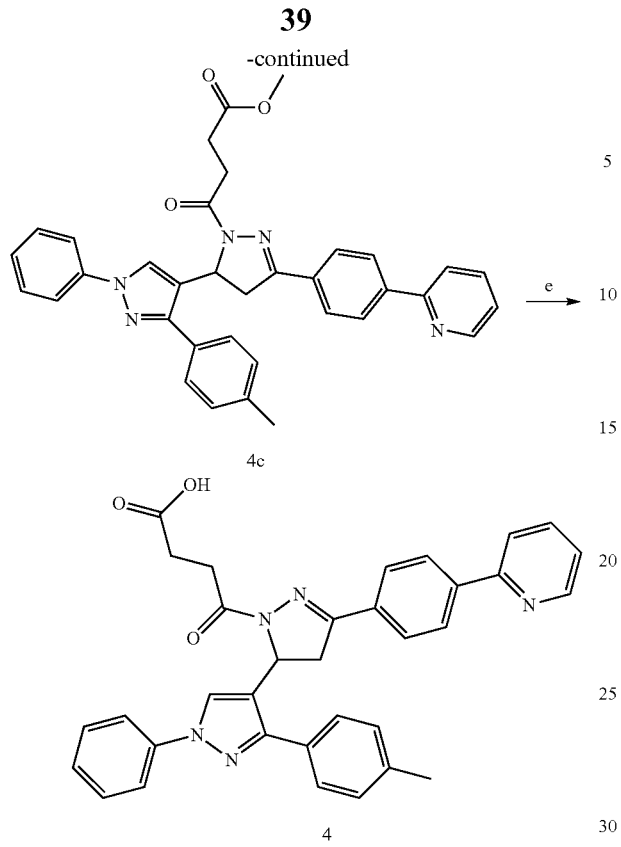

Scheme 3 depicts a route for synthesizing compound 4.

Example 13-4a 1-(4-(pyridin-2-yl)phenyl)ethanone

A mixture of (4-acetylphenyl)boronic acid (500 mg, 3.7 mmol), 2-bromopyridine (560 mg, 3.1 mmol), Pd(PPh$_3$)$_4$ (350 mg, 0.31 mmol), and K$_2$CO$_3$ (860 mg, 6.2 mml) in a mixture of dioxane and water (v/v=5:1, 50 mL) under N$_2$ was refluxed for 4 h. The mixture was evaporated to remove the solvent under reduced pressure. The residue was mixed with EtOAc (50 mL), and the mixture was washed with water and brine. The organic phase was dried with Na$_2$SO$_4$, filtered, and concentrated. The residue was purified by column chromatography (PE/EA=5:1) to give the desired product (550 mg, 90% yield). $^1$H NMR (400 MHz, DMSO-d6): δ 8.74 (d, J=4.8 Hz, 1H), 8.12-8.05 (m, 4H), 7.8 (d, J=3.6 Hz, 2H), 7.3-7.26 (m, 1H), 2.65 (s, 3H). ESIMS (m/z) for C$_{13}$H$_{12}$NO$^+$ [M+H]$^+$: calculated 198.08, found 198.10.

Example 14-4b 3-(1-phenyl-3-(p-tolyl)-1H-pyrazol-4-yl)-1-(4-(pyridin-2-yl)phenyl)prop-2-en-1-one This compound was prepared essentially by the method of Example 3 (300 mg, 74% yield). $^1$H NMR (400 MHz, CDCl$_3$): δ 8.75 (d, J=5.2 Hz, 1H), 8.37 (s, 1H), 8.14-8.12 (d, J=8.0 Hz, 2H), 8.09-8.06 (d, J=7.6 Hz, 2H), 7.95-7.91 (d, J=15.6 Hz, 1H), 7.82 (m, 4H), 7.62 (d, J=7.6 Hz, 2H), 7.52-7.48 (m, 2H), 7.40-7.36 (m, 1H), 7.35-7.32 (d, J=8.4 Hz, 1H), 7.30 (m, 3H), 2.43 (s, 3H). ESIMS (m/z) for C$_{30}$H$_{24}$N$_3$O$^+$ [M+H]$^+$: calculated 442.18, found 442.20.

Example 15-4c 5-(4-(pyridin-2-yl)phenyl)-3'-(p-tolyl)-3,4-dihydro-1'H,2H-3,4'-bipyrazole This compound was prepared essentially by the method of Example 4 (242 mg, 78% yield). $^1$H NMR (400 MHz, CDCl$_3$): δ 8.70 (s, 1H), 8.04 (m, 3H), 7.08-7.72 (m, 7H), 7.62 (m, 2H), 7.42 (m, 3H), 6.03 (m, 1H), 5.19 (m, 1H), 3.56-3.50 (m, 1H), 3.16-3.10 (m, 1H), 2.41 (s, 3H). ESIMS (m/z) for C$_{30}$H$_{26}$N$_5$$^+$ [M+H]$^+$: calculated 456.21, found 456.20.

Example 16-4d

Methyl-4-oxo-4-(1'-phenyl-5-(4-(pyridin-2-yl)phenyl)-3'-(p-tolyl)-1H,1'H[3,4'-bipyrazol]-2(5H)-yl)butanoate This compound was prepared essentially by the method of Example 5 (182 mg, 60% yield). $^1$H NMR (400 MHz, DMSO-d6): δ 8.72 (d, J=4.8 Hz, 1H), 8.04-8.02 (d, J=8.4 Hz, 2H), 7.95 (s, 1H), 7.78-7.75 (m, 6H), 7.65-7.63 (d, J=8.0 Hz, 2H), 7.39 (m, 2H), 7.23 (m, 6H), 5.98-5.94 (dd, J=11.2, 4.0 Hz, 1H), 3.70 (s, 3H), 3.67 (m, 1H), 3.46-3.38 (m, 1H), 3.16-3.15 (m, 2H), 3.12-3.00 (m, 1H), 2.74 (m, 1H), 2.38 (s, 3H). ESIMS (m/z) for C$_{35}$H$_{32}$N$_5$O$_3$$^+$ [M+H]$^+$: calculated 570.24, found 570.20.

Example 17-4

4-oxo-4-(1'-phenyl-5-(4-(pyridin-2-yl)phenyl)-3'-(p-tolyl)-1H,1'H-[3,4'-bipyrazol]-2(5H)-yl)butanoic acid This compound was prepared essentially by the method of Example 6 (59 mg, 41% yield). $^1$H NMR (400 MHz, DMSO-d6): δ 8.69 (d, J=4.0 Hz, 1H), 8.30 (s, 1H), 8.18 (d, J=8.4 Hz, 2H), 8.02 (d, J=8.4 Hz, 2H), 7.92-7.82 (m, 5H), 7.69 (d, J=8.0 Hz, 2H), 7.49-7.45 (m, 2H), 7.40-7.37 (m, 1H), 7.31-7.26 (m, 2H), 5.76-5.72 (dd, J=11.6, 4.8 Hz, 1H), 3.93 (m, 1H), 3.26-3.21 (m, 1H), 2.93 (m, 1H) 2.57-2.54 (m, 1H), 2.36 (s, 3H); $^{13}$C NMR (100 MHz, DMSO-d6): 174.51, 169.63, 155.54, 154.14, 150.14, 149.72, 140.49, 139.87, 137.82, 132.23, 129.92, 129.67, 128.28, 127.54, 127.16, 126.86, 126.60, 123.55, 120.94, 118.62, 52.77, 42.40, 29.34, 29.07, 21.33. ESIMS (m/z) for C$_{34}$H$_{30}$N$_5$O$_3$$^+$ [M+H]$^+$: calculated 556.23, found 556.20.

Example 18-5a 1-isopropyl-2-(1-(p-tolyl)ethylidene)hydrazine

This compound was prepared essentially by the method of Example 1 (0.9 g, 65% yield). ESIMS (m/z) for C$_{12}$H$_{19}$N$_2$$^+$ [M+H]$^+$: calculated 191.15, found 191.10.

Example 19-5b 1-isopropyl-3-(p-tolyl)-1H-pyrazole-4-carbaldehyde

This compound was prepared essentially by the method of Example 2 (460 mg, 37% yield). $^1$H NMR (400 MHz, CDCl$_3$): δ 9.93 (s, 1H), 8.06 (s, 1H), 7.61 (d, J=8.0 Hz, 2H), 7.28 (d, J=8.0 Hz, 2H), 4.56 (M, 1H), 2.40 (s, 3H), 1.58 (d, J=6.8 Hz, 6H). ESIMS (m/z) for $C_{14}H_{17}N_2O^+$ [M+H]$^+$: calculated 229.13, found 229.10.

Example 20-5c 3-(1-isopropyl-3-(p-tolyl)-1H-pyrazol-4-yl)-1-(4-methoxyphenyl)prop-2-en-1-one This compound was prepared essentially by the method of Example 3 (569 mg, 90% yield). $^1$H NMR (400 MHz, CDCl$_3$): (7.96 (d, J=8.8 Hz, 2H), 7.85 (d, J=8.0 Hz, 2H), 7.52 (d, J=8.0 Hz, 2H), 6.96 (d, J=8.8 Hz, 2H), 4.56 (M, 1H), 3.87 (s, 3H), 2.40 (s, 3H), 1.59 (d, J=6.4 Hz, 6H). ESIMS (m/z) for $C_{23}H_{25}N_2O_2^+$ [M+H]$^+$: calculated 361.18, found 361.20.

Example 21-5d

1'-isopropyl-5-(4-methoxyphenyl)-3'-(p-tolyl)-3,4-dihydro-1'H,2H-3,4'-bipyrazole This compound was prepared essentially by the method of Example 4 (255 mg, 74% yield). $^1$H NMR (400 MHz, CDCl$_3$): δ 7.62 (d, J=8.4 Hz, 2H), 7.49 (m, 3H), 7.24 (d, J=8.0 Hz, 2H), 6.93 (d, J=8.8 Hz, 2H), 5.06-5.02 (m, 1H), 4.50-4.47 (m, 1H), 3.83 (s, 3H), 3.71 (m, 1H), 3.42-3.35 (m, 1H), 3.02-2.96 (m, 1H), 2.38 (s, 3H), 1.52 (d, J=6.4 Hz, 6H). ESIMS (m/z) for $C_{23}H_{27}N_4O^+$ [M+H]$^+$: calculated 375.21, found 375.20.

Example 22-5e 4-(1'-isopropyl-5-(4-methoxyphenyl)-3'-(p-tolyl)-1H,1'H-[3,4'-bipyrazol]-2(5H)-yl)-4-oxobutanoate This compound was prepared essentially by the method of Example 5 (120 mg, 36% yield). $^1$H NMR (400 MHz, CDCl$_3$): (7.58 (d, J=8.8 Hz, 1H), 7.20 (d, J=8.0 Hz, 2H), 7.32 (s, 1H), 7.17 (d, J=8.0 Hz, 2H), 6.88 (d, J=8.8 Hz, 2H), 5.84-5.80 (dd, J=11.6, 4.0 Hz, 1H), 4.44-4.41 (m, 1H), 3.84 (s, 3H), 3.69 (s, 3H), 3.55-3.48 (m, 1H), 3.28-3.22 (m, 1H), 3.01-2.95 (m, 2H), 2.81-2.67 (m, 2H), 2.34 (s, 3H), 1.48 (d, J=6.4 Hz, 6H). ESIMS (m/z) for $C_{28}H_{33}N_4O_4^+$ [M+H]$^+$: calculated 489.24, found 489.20.

Example 23-5

4-(1'-isopropyl-5-(4-methoxyphenyl)-3'-(p-tolyl)-1H,1'H-[3,4'-bipyrazol]-2(5H)-yl)-4-oxobutanoic acid This compound was prepared essentially by the method of Example 6 (87 mg, 77% yield). $^1$H NMR (400 MHz, CDCl$_3$): δ 7.58 (d, J=8.8 Hz, 1H), 7.51-7.49 (d, J=8.0 Hz, 2H), 7.27 (s, 1H), 7.17 (d, J=8.0 Hz, 2H), 6.91-6.88 (d, J=8.8 Hz, 2H), 5.83-5.79 (dd, J=11.2, 4.0 Hz, 1H), 4.45-4.41 (m, 1H), 3.84 (s, 3H), 3.58-3.51 (dd, J=17.2, 11.2 Hz, 1H), 3.23-3.20 (m, 1H), 3.10-3.00 (m, 2H), 2.80-2.73 (m, 2H), 2.34 (s, 3H), 1.48 (d, J=6.8 Hz, 6H); $^{13}$C NMR (100 MHz, CDCl$_3$): δ 161.60, 150.16, 139.88, 137.91, 130.24, 129.32, 129.26, 128.40, 128.15, 126.30, 125.80, 123.66, 121.92, 119.02, 114.12, 55.40, 52.69, 42.09, 29.04, 21.26. ESIMS (m/z) for $C_{27}H_{31}N_4O_4^+$ [M+H]$^+$: calculated 475.23, found 475.20.

Example 24-6e (7)

Methyl 3-(5-(4-methoxyphenyl)-1'-phenyl-3'-(p-tolyl)-2,5-dihydro-1H,1'H-[3,4'-bipyrazole]-2-carbonyl)benzoate This compound was prepared essentially by the method of Example 5. $^1$H NMR (400 MHz, CDCl$_3$): δ 8.80 (s, 1H), 8.19 (m, 2H), 7.87 (s, 1H), 7.68 (d, J=7.2 Hz, 4H), 7.59-7.52 (m, 3H), 7.39 (t, J=7.6 Hz, 2H), 7.24 (m, 2H), 6.89 (d, J=8.8 Hz, 2H), 6.09 (m, 1H), 3.96 (s, 3H), 3.83 (s, 3H), 3.68-3.61 (dd, J=17.6 11.6 Hz, 1H), 3.17-3.12 (dd, J=17.2 3.6 Hz, 1H), 2.38 (s, 3H). ESIMS (m/z) for $C_{35}H_{31}N_4O_4^+$ [M+H]$^+$: calculated 571.23, found 571.20.

Example 25-6

3-(5-(4-methoxyphenyl)-1'-phenyl-3'-(p-tolyl)-2,5-dihydro-1H,1'H-[3,4'-bipyrazole]-2-carbonyl)benzoic acid This compound was prepared essentially by the method of Example 6. $^1$H NMR (400 MHz, CDCl$_3$): δ 8.88 (s, 1H), 8.25 (s, 2H), 7.88 (s, 1H), 7.69 (d, J=7.6 Hz, 4H), 7.58 (m, 3H), 7.39 (m, 2H), 7.24 (m, 2H), 6.89 (d, J=8.4 Hz, 2H), 6.11 (m, 1H), 3.82 (m, 1H), 3.17 (m, 1H), 2.38 (s, 3H); $^{13}$C NMR (100 MHz, CDCl$_3$): 161.58, 155.52, 150.65, 139.89, 137.97, 134.94, 132.44, 132.17, 129.33, 129.27, 128.46, 128.36, 128.04, 126.38, 125.73, 123.73, 122.19, 119.13, 114.16, 55.37, 53.66, 41.44, 21.27. ESIMS (m/z) for $C_{34}H_{29}N_4O_4^+$ [M+H]$^+$: calculated 557.21, found 557.20.

Example 26-8a 1-(1-(4-chlorophenyl)ethylidene)-2-phenylhydrazine

This compound was prepared essentially by the method of Example 1 (yellow solid, 1.7 g, 90% yield). $^1$H NMR (400 MHz, CDCl$_3$): δ 7.72-7.70 (d, J=8.8 Hz, 2H), 7.69-7.25 (m, 5H), 7.17 (d, J=7.6 Hz, 2H), 6.90-6.87 (t, J=7.2 Hz, 1H), 2.38 (s, 3H). ESIMS (m/z) for $C_{14}H_{14}ClN_2^+$ [M+H]$^+$: calculated 225.08, found 225.10.

Example 27-8b 3-(4-chlorophenyl)-1-phenyl-1H-pyrazole-4-carbaldehyde

This compound was prepared essentially by the method of Example 2 (light yellow solid, 1.44 g, 68% yield). $^1$H NMR (400 MHz, CDCl$_3$): δ 10.04 (s, 1H), 8.53 (s, 1H), 7.84-7.82 (d, J=8.4 Hz, 2H), 7.80-7.78 (d, J=8.4 Hz, 2H), 7.53-7.48 (m, 4H), 7.46-7.41 (t, J=7.6 Hz, 1H). ESIMS (m/z) for $C_{16}H_{12}ClN_2O^+$ [M+H]$^+$: calculated 283.06, found 283.10.

Example 28-8c 3-(3-(4-chlorophenyl)-1-phenyl-1H-pyrazol-4-yl)-1-(4-methoxyphenyl)prop-2-en-1-one This compound was prepared essentially by the method of Example 3 (light yellow solid, 1.76 g, 83% yield). $^1$H NMR (400 MHz, CDCl$_3$): δ 8.34 (s, 1H), 7.99-7.97 (d, J=8.8 Hz, 2H), 7.86-7.82 (d, J=15.6 Hz, 1H), 7.80-7.78 (d, J=7.6 Hz, 2H), 7.68-7.66 (d, J=8.4 Hz, 1H), 7.52-7.46 (m, 4H), 7.40-

7.35 (m, 2H), 6.99-6.96 (d, J=8.8 Hz, 2H), 3.89 (s, 3H). ESIMS (m/z) for $C_{25}H_{20}ClN_2O_2^+$ [M+H]$^+$: calculated 415.11, found 415.10.

Example 29-8d

3'-(4-chlorophenyl)-5-(4-methoxyphenyl)-1'-phenyl-3,4-dihydro-1'H,2H-3,4'-bipyrazole This compound was prepared essentially by the method of Example 4 (white solid, 672 mg, 86% yield). $^1$H NMR (400 MHz, CDCl$_3$): δ 8.03 (s, 1H), 7.72-7.67 (m, 3H), 7.63-7.61 (m, 1H), 7.46-7.42 (m, 4H), 7.31-7.27 (m, 1H), 6.93-6.91 (d, J=8.8 Hz, 2H), 5.13 (m, 1H), 3.68-3.62 (m, 1H), 3.17-3.12 (m, 1H). ESIMS (m/z) for $C_{25}H_{22}ClN_4O^+$ [M+H]$^+$: calculated 429.14, found 429.10.

Example 30-8e

Methyl 3-(3'-(4-chlorophenyl)-5-(4-methoxyphenyl)-1'-phenyl-3,4-dihydro-1'H, 2H-[3,4'-bipyrazole]-2-carbonyl)benzoate This compound was prepared essentially by the method of Example 5 (white solid, 340 mg, 62% yield). $^1$H NMR (400 MHz, CDCl$_3$): δ 8.80 (s, 1H), 8.21-8.27 (m, 2H), 7.89 (s, 1H), 7.78-7.76 (d, J=8.0 Hz, 2H), 7.68-7.66 (d, J=7.6 Hz, 2H), 7.60-7.58 (m, 2H), 7.56-7.52 (m, 1H), 7.42-7.39 (m, 4H), 7.26 (m, 1H), 6.92-6.90 (d, J=8.8 Hz, 2H), 6.07-6.03 (m, 1H), 3.96 (s, 3H), 3.84 (s, 3H), 3.71-3.64 (m, 1H), 3.16-3.11 (m, 1H). ESIMS (m/z) for $C_{34}H_{28}ClN_4O_4^+$ [M+H]$^+$: calculated 591.17, found 591.20.

Example 31-8

3-(3'-(4-chlorophenyl)-5-(4-methoxyphenyl)-1'-phenyl-3,4-dihydro-1'H,2H-[3,4'-bipyrazole]-2-carbonyl)benzoic acid This compound was prepared essentially by the method of Example 6 (white solid, 50 mg, 87% yield). $^1$H NMR (400 MHz, CDCl$_3$): δ 8.85 (s, 1H), 8.24-8.23 (d, J=7.6 Hz, 2H), 7.90 (s, 1H), 7.78-7.76 (d, J=8.0 Hz, 2H), 7.69-7.67 (d, J=8.0 Hz, 2H), 7.60-7.58 (m, 3H), 7.42-7.38 (m, 4H), 7.26 (m, 1H), 6.92-6.90 (d, J=8.8 Hz, 2H), 6.08-6.04 (m, 1H), 3.82 (s, 3H), 3.73-3.65 (m, 1H), 3.17-3.12 (m, 1H); $^{13}$C NMR (100 MHz, CDCl$_3$): (170.27, 165.08, 161.70, 155.43, 149.47, 139.73, 135.09, 134.75, 134.27, 132.52, 132.14, 131.72, 129.84, 129.33, 128.85, 128.45, 128.06, 126.66, 126.01, 123.56, 122.45, 119.20, 114.27, 55.38, 53.48, 41.52, 29.69. ESIMS (m/z) for $C_{33}H_{26}ClN_4O_4^+$ [M+H]$^+$: calculated 577.16, found 577.20.

Example 32-9a 1-benzyl-2-(1-(p-tolyl)ethylidene)hydrazine

NaOAc (1.64 g, 20 mmol) was slowly added to the mixture of benzylhydrazine dihydrochloride (2.32 g, 12 mmol) in ethanol (20 mL) at 0° C. in an ice bath. The mixture was warmed to room temperature and then 4'-methylacetophenone (1.34 g, 10 mmol) was added. The mixture was stirred for 3 h. The mixture was cooled to −15° C., and the precipitate was filtered and washed with cold ethanol (15 mL). The filtrate was concentrated to dryness to give crude product as yellow oil (2.8 g), which was used for next steps without further purification. ESIMS (m/z) for $C_{16}H_{19}N_2^+$ [M+H]$^+$: calculated 239.15, found 239.10.

Example 33-9b 1-benzyl-3-(p-tolyl)-1H-pyrazole-4-carbaldehyde

This compound was prepared essentially by the method of Example 2 (yellow oil, 1.4 g, 41% yield for two steps). $^1$H NMR (400 MHz, CDCl$_3$): δ 9.84 (s, 1H), 7.85 (s, 1H), 7.56-7.54 (d, J=8.0 Hz, 2H), 7.33-7.29 (m, 3H), 7.22-7.24 (m, 2H), 7.21-7.19 (m, 2H), 5.28 (s, 2H), 2.34 (s, 3H). ESIMS (m/z) for $C_{18}H_{17}N_2O^+$ [M+H]$^+$: calculated 277.13, found 277.10.

Example 34-9c 3-(1-benzyl-3-(p-tolyl)-1H-pyrazol-4-yl)-1-(4-methoxyphenyl)-prop-2-en-1-one This compound was prepared essentially by the method of Example 3. The product was purification by column chromatography (PE/EA=4:1) to give product as a light yellow solid (1.4 g, 63% yield). $^1$H NMR (400 MHz, CDCl$_3$): δ 7.90 (d, J=8.0 Hz, 2H), 7.83-7.79 (d, J=15.6 Hz, 1H), 7.53-7.51 (d, J=8.0 Hz, 2H), 7.35-7.28 (m, 4H), 7.25-7.18 (m, 3H), 6.90-6.88 (d, J=8.8 Hz, 2H), 5.32 (s, 2H), 2.38 (s, 3H). ESIMS (m/z) for $C_{27}H_{25}N_2O_2^+$ [M+H]$^+$: calculated 409.18, found 409.20.

Example 35-9d

1'-benzyl-5-(4-methoxyphenyl)-3'-(p-tolyl)-3,4-dihydro-1'H,2H-3,4'-bipyrazole

This compound was prepared essentially by the method of Example 4. The mixture was evaporated to dryness to give crude product as light solid (1.4 g crude). $^1$H NMR (400 MHz, CDCl$_3$): δ 7.93-7.91 (d, J=8.4 Hz, 2H), 7.84-7.82 (d, J=8.8 Hz, 2H), 7.74 (s, 1H), 7.58-7.42 (m, 4H), 7.31-7.30 (m, 1H), 7.27-7.22 (m, 2H), 6.90-6.89 d, J=8.8 Hz, 2H), 5.31 (s, 2H), 5.06-5.01 (m, 1H), 3.82 (s, 3H), 3.40-3.30 (m, 1H), 2.96-2.91 (m, 1H), 2.38 (s, 3H). ESIMS (m/z) for $C_{27}H_{27}N_4O^+$ [M+H]$^+$: calculated 423.21, found 423.20.

Example 36-9e

Methyl 3-(1'-benzyl-5-(4-methoxyphenyl)-3'-(p-tolyl)-3,4-dihydro-1'H,2H-[3,4'-bipyrazole]-2-carbonyl)benzoate This compound was prepared essentially by the method of Example 5 (85 mg, 31% yield). $^1$H NMR (400 MHz, CDCl$_3$): δ 8.74 (s, 1H), 8.18 (m, 2H) 7.62-7.61 (m, 2H) 7.56-7.51 (m, 3H), 7.36-7.31 (m, 4H), 7.28-7.23 (m, 2H), 7.23-7.21 (d, J=8.0 Hz, 2H), 6.91-6.88 (d, J=8.8 Hz, 2H), 6.04-6.01 (m, 1H), 5.29 (s, 2H), 3.98 (s, 3H), 3.85 (s, 3H), 3.65-3.58 (m, 1H), 3.12-3.06 (m, 1H), 2.37 (s, 3H). ESIMS (m/z) for $C_{36}H_{33}N_4O_4^+$ [M+H]$^+$: calculated 585.24, found 585.20.

Example 37-9

3-(1'-benzyl-5-(4-methoxyphenyl)-3'-(p-tolyl)-3,4-dihydro-1'H,2H-[3,4'-bipyrazole]-2-carbonyl)benzoic acid This compound was prepared essentially by the method of Example 6. $^1$H NMR (400 MHz, CDCl$_3$): δ 8.69 (s, 1H), 8.114-8.07 (m, 2H) 7.51-7.43 (m, 5H) 7.27-7.22 (m, 4H), 7.21 (m, 2H), 7.18-7.11 (m, 2H), 6.80-6.78 (d, J=8.8 Hz, 2H), 5.94-5.92 (m, 1H), 5.20 (s, 2H), 3.73 (s, 3H), 3.55-3.48 (m, 1H), 3.02-2.96 (m, 1H), 2.27 (s, 3H). ESIMS (m/z) for $C_{35}H_{31}N_4O_4^+$ [M+H]$^+$: calculated 571.23, found 571.20.

Example 38-10a 1-(4-methoxyphenyl)-2-(1-(p-tolyl)ethylidene)hydrazine

NaOAc (0.82 g, 10 mmol) was slowly added to the mixture of (4-methoxyphenyl) hydrazine hydrochloride (1.04 g, 6 mmol) in ethanol (20 mL) at 0° C. in an ice bath. The mixture was warmed to room temperature and then 4'-methylacetophenone (0.67 g, 5 mmol) was added and the mixture was stirred for 3 h. The mixture was cooled to −15° C. The precipitate was filtered and washed with cold ethanol (15 mL) to give the product as a brown solid (1.03 g, 81% yield). $^1$H NMR (400 MHz, CDCl$_3$): δ 7.88 (d, J=7.2 Hz, 1H), 7.18-7.16 (d, J=7.6 Hz, 4H), 7.13-7.12 (m, 2H), 6.88 (d, J=7.6 Hz, 2H), 3.78 (s, 3H), 2.36 (s, 3H), 2.21 (s, 3H). ESIMS (m/z) for $C_{16}H_{19}N_2O^+$ [M+H]$^+$: calculated 255.14, found 255.10.

Example 39-10b 1-(4-methoxyphenyl)-3-(p-tolyl)-1H-pyrazole-4-carbaldehyde

This compound was prepared essentially by the method of Example 2 (yellow solid, 410 mg, 35% yield). $^1$H NMR (400 MHz, CDCl$_3$): δ 10.02 (s, 1H), 8.42 (s, 1H), 7.71-7.67 (m, 4H), 7.31-7.26 (m, 2H), 7.01 (d, J=9.2 Hz, 2H), 3.85 (s, 3H), 2.42 (s, 3H). ESIMS (m/z) for $C_{18}H_{17}N_2O_2^+$ [M+H]$^+$: calculated 293.12, found 293.10.

Example 40-10c 1-(4-methoxyphenyl)-3-(1-(4-methoxyphenyl)-3-(p-tolyl)-1H-pyrazol-4-yl)-prop-2-en-1-one This compound was prepared essentially by the method of Example 3 (yellow solid, 424 mg, 71% yield). $^1$H NMR (400 MHz, CDCl$_3$): δ 8.25 (s, 1H), 7.98-7.96 (d, J=9.2 Hz, 2H), 7.89-7.86 (d, J=15.6 Hz, 1H), 7.01-7.68 (d, J=9.2 Hz, 2H), 7.61-7.59 (d, J=8.0 Hz, 2H), 7.36-7.33 (d, J=15.6 Hz, 1H), 7.30-7.28 (m, 2H), 7.02-6.99 (d, J=9.2 Hz, 1H), 6.97-6.94 (d, J=8.8 Hz, 2H), 3.82 (m, 1H), 3.89 (s, 3H), 3.87 (s, 3H), 2.43 (s, 3H). ESIMS (m/z) for $C_{27}H_{25}N_2O_3^+$ [M+H]$^+$: calculated 425.18, found 425.20.

Example 41-10d

1'-(4-methoxyphenyl)-3',5-di-p-tolyl-3,4-dihydro-1'H,2H-3,4'-bipyrazole

This compound was prepared essentially by the method of Example 4 (white solid, 310 mg, 73% yield). $^1$H NMR (400 MHz, CDCl$_3$): δ 7.91 (s, 1H), 7.71-7.58 (m, 6H), 7.28 (m, 1H), 6.96-6.90 (m, 4H), 5.13-5.09 (m, 1H), 3.83 (s, 6H), 3.47-3.41 (m, 1H), 3.08-3.02 (m, 1H), 2.41 (s, 3H). ESIMS (m/z) for $C_{27}H_{27}N_4O^+$ [M+H]$^+$: calculated 423.21, found 423.20.

Example 42-10e

Methyl 3-(1',5-bis(4-methoxyphenyl)-3'-(p-tolyl)-3,4-dihydro-1'H,2H-[3,4'-bipyrazole]-2-carbonyl)benzoate This compound was prepared essentially by the method of Example 5 (white solid, 286 mg, 65% yield). $^1$H NMR (400 MHz, CDCl$_3$): δ 8.80 (s, 1H), 8.22-8.17 (m, 2H), 7.77 (s, 1H), 7.69-7.67 (m, 2H), 7.59-7.52 (m, 5H), 7.23 (m, 1H), 6.92-6.88 (m, 4H), 6.11 (m, 1H), 3.96 (s, 3H), 3.83 (s, 3H), 3.81 (s, 3H), 3.68-3.61 (m, 1H), 3.17-3.11 (m, 1H), 2.38 (s, 3H). ESIMS (m/z) for $C_{36}H_{33}N_4O_5^+$ [M+H]$^+$: calculated 601.24, found 601.20.

Example 43-10

3-(1',5-bis(4-methoxyphenyl)-3'-(p-tolyl)-3,4-dihydro-1'H,2H-[3,4'-bipyrazole]-2-carbonyl)benzoic acid This compound was prepared essentially by the method of Example 6 (white solid, 50 mg, 89% yield). $^1$H NMR (400 MHz, CDCl$_3$): δ 8.86 (s, 1H), 8.24-8.22 (d, J=6.4 Hz, 2H), 7.78 (s, 1H), 7.78-7.68 (d, J=8.0 Hz, 2H), 7.66-7.57 (m, 5H), 7.25 (m, 2H), 6.92-6.88 (m, 2H), 6.12-6.08 (m, 1H), 3.82 (s, 3H), 3.81 (s, 3H), 3.68-3.62 (m, 1H), 3.17-3.12 (m, 1H), 2.38 (s, 3H). $^{13}$C NMR (100 MHz, CDCl$_3$): δ 170.33, 165.04, 161.58, 158.27, 155.57, 150.18, 137.82, 135.14, 134.97, 133.73, 132.41, 132.18, 130.42, 129.30, 128.96, 128.46, 128.36, 128.01, 125.86, 123.77, 121.72, 120.83, 114.43, 114.16, 55.52, 55.37, 53.70, 41.47, 21.25. ESIMS (m/z) for $C_{35}H_{31}N_4O_5^+$ [M+H]$^+$: calculated 587.22, found 587.20.

Scheme 4

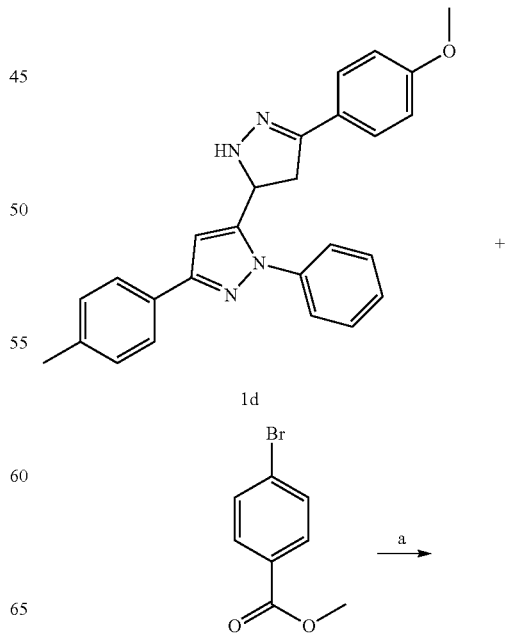

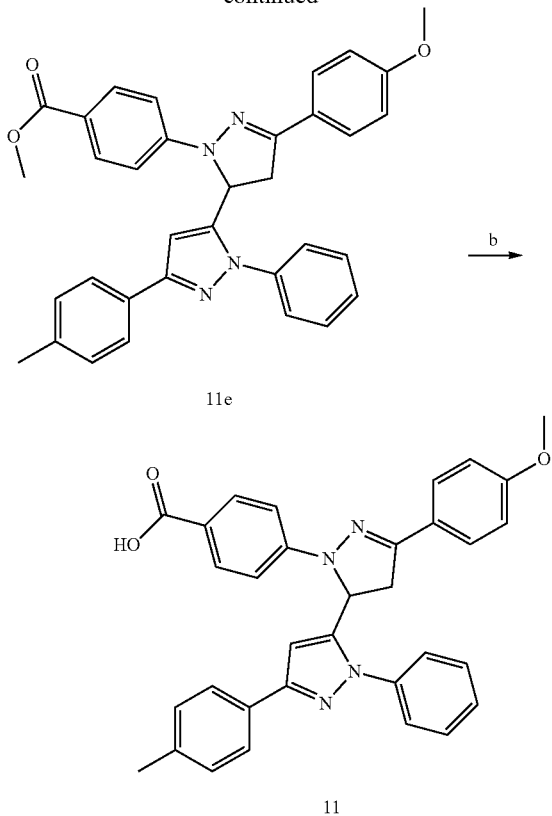

Scheme 4 depicts a route for synthesizing compound 11.

Example 44-11e

Methyl 4-(5-(4-methoxyphenyl)-2'-phenyl-5'-(p-tolyl)-3,4-dihydro-2H,2'H-[3,3'-bipyrazol]-2-yl)benzoate A mixture of methyl 4-bromobenzoate (54 mg, 0.25 mmol), 5-(4-methoxyphenyl)-2'-phenyl-5'-(p-tolyl)-3,4-dihydro-2H,2'H-3,3'-bipyrazole (100 mg, 0.25 mmol), Pd$_2$(dba)$_3$ (46 mg, 0.05 mmol), xPhos (46 mg, 0.1 mmol), and Cs$_2$CO$_3$ (163 mg, 0.5 mml) in anhydrous dioxane (25 mL) under N$_2$ was refluxed for 3 h. The solvent was removed. EtOAc (20 mL) was added. The mixture was washed with water and brine. The organic phase was dried with Na$_2$SO$_4$, filtered and concentrated. The residue was purified by prep.-HPLC to give the desired product as white solid (30.4 mg, 22.4% yield). $^1$H NMR (400 MHz, CDCl$_3$): δ 7.86 (d, J=8.8 Hz, 2H), 7.70-7.66 (m, 5H), 7.60 (m, 2H), 7.38-7.34 (m, 4H), 7.25-7.19 (m, 1H), 7.03 (d, J=8.8 Hz, 2H), 6.92 (d, J=8.8 Hz, 2H), 5.60-5.55 (m, 1H), 3.84 (m, 1H), 3.83 (s, 6H), 2.31-2.25 (dd, J=16.8 Hz, 5.6 Hz, 1H), 2.45 (s, 3H). ESIMS (m/z) for C$_{34}$H$_{34}$N$_4$O$_3^+$ [M+H]$^+$: calculated 543.23, found 543.2.

Example 45-11

4-(5-(4-methoxyphenyl)-2'-phenyl-5'-(p-tolyl)-3,4-dihydro-2H,2'H-[3,3'-bipyrazol]-2-yl)benzoic acid 11 was synthesized by the same method as 1. $^1$H NMR (400 MHz, DMSO-d$_6$): δ 8.27 (s, 1H), 7.83-7.81 (d, J=8.0 Hz, 2H), 7.73-7.67 (m, 6H), 7.45-7.41 (m, 2H), 7.34-7.32 (d, J=7.6 Hz, 2H), 7.28-7.24 (t, J=7.6 Hz, 1H), 7.02-6.96 (m, 4H), 5.64-5.60 (m, 1H), 4.08-4.01 (m, 1H), 3.80 (s, 3H), 3.32 (m, 1H), 2.38 (s, 3H). ESIMS (m/z) for C$_{33}$H$_{29}$N$_4$O$_3^+$ [M+H]$^+$: calculated 529.22, found 529.2.

Example 46-12a (E)-3-(2-(1-(p-tolyl) ethylidene) hydrazinyl) pyridine

Crude 12a (2.5 g without purification) was synthesized by the same method as 1a. ESIMS (m/z) for C$_{14}$H$_{16}$N$_3^+$ [M+H]$^+$: calculated 226.3, found 226.2.

Example 47-12b 1-(pyridin-3-yl)-3-(p-tolyl)-1H-pyrazole-4-carbaldehyde 12b (570 mg) was synthesized by the same method as 1b. ESIMS (m/z) for C$_{16}$H$_{14}$N$_3$O$^+$ [M+H]$^+$: calculated 264.3, found 264.1.

Example 48-12c (E)-1-(4-methoxyphenyl)-3-(1-(pyridin-3-yl)-3-(p-tolyl)-1H-pyrazol-4-yl) prop-2-en-1-one (12c) 12c (410 mg, 48% yield) was synthesized by the same method as 1c. $^1$H NMR (400 MHz, CDCl3): δ 9.08 (s, 1H), 8.60 (d, J=4.8 Hz, 1H), 8.37 (s, 1H), 8.17 (d, J=8.0 Hz, 1H), 7.98 (d, J=8.8 Hz, 2H), 7.86 (d, J=15.6 Hz, 1H), 7.60 (d, J=8.0 Hz, 2H), 7.43-7.46 (m, 1H), 7.39 (d, J=15.6 Hz, 1H), 7.31 (d, J=4.4 Hz, 2H), 6.96 (d, J=8.4 Hz, 2H), 3.88 (s, 3H), 2.43 (s, 3H). ESIMS (m/z) for C$_{25}$H$_{22}$N$_3$O$_2^+$ [M+H]$^+$: calculated 396.5, found 396.1.

Example 49-12d (5-(4-methoxyphenyl)-1'-(pyridin-3-yl)-3'-(p-tolyl)-3,4-dihydro-1'H, 2H-3, 4'-bipyrazole 12d (270 mg, 63% yield) was synthesized by the same method as 1d. ESIMS (m/z) for C$_{25}$H$_{24}$N$_5$O$^+$ [M+H]$^+$: calculated 410.5, found 410.2.

Example 50-12e

Methyl 3-(5-(4-methoxyphenyl)-1'-(pyridin-3-yl)-3'-(p-tolyl)-3, 4-dihydro-1'H, 2H-[3, 4'-bipyrazole]-2-carbonyl) benzoate 12e (62 mg, 45% yield) was synthesized by the same method as 1e. ESIMS (m/z) for C$_{34}$H$_{30}$N$_5$O$_4^+$ [M+H]$^+$: calculated 572.6, found 572.2.

Example 51-12

3-(5-(4-methoxyphenyl)-1'-(pyridin-3-yl)-3'-(p-tolyl)-3, 4-dihydro-1'H, 2H-[3, 4'-bipyrazole]-2-carbonyl) benzoic acid 12 (35 g, 57% yield) was synthesized by the same method as 1. $^1$H NMR (400 MHz, d$_6$-DMSO): δ 9.15 (s, 1H), 8.65 (s, 1H), 8.50 (s, 2H), 8.28 (d, J=8.0 Hz, 1H), 8.08 (t, J=8.0 Hz, 2H), 7.50-7.74 (m, 6H), 7.32 (d, J=8.0 Hz, 2H), 7.00 (d, J=8.0 Hz, 2H), 7.88-7.92 (m, 1H), 3.92-3.99 (m, 1H), 3.79

(s, 3H), 3.25-3.27 (m, 1H), 2.38 (s, 3H). $^{13}$C NMR (100 MHz, d$_6$-DMSO): δ 161.5, 155.6, 151.1, 147.6, 140.3, 138.1, 135.4, 131.8, 131.1, 130.3, 129.7, 128.9, 128.6, 127.5, 126.1, 124.6, 124.3, 124.1, 114.7, 55.8, 53.5, 42.3, 21.4. ESIMS (m/z) for C$_{33}$H$_{28}$N$_5$O$_4^+$ [M+H]$^+$: calculated 558.6, found 558.2.

Example 52-13a (E)-1-(1-(4-methoxyphenyl) ethylidene)-2-phenyl-hydrazine 13a (6.8 g, 85% yield) was synthesized by the same method as 1a. ESIMS (m/z) for C$_{15}$H$_{17}$N$_2$O$^+$ [M+H]$^+$: calculated 241.3, found 241.2.

Example 53-13b 3-(4-methoxyphenyl)-1-phenyl-1H-pyrazole-4-carb-aldehyde 13b (3.1 g, 89% yield) was synthesized by the same method as 1b. $^1$H NMR (400 MHz, CDCl$_3$): δ 10.04 (s, 1H), 8.52 (s, 1H), 7.78-7.81 (m, 4H), 7.49-7.53 (m, 2H), 7.39 (t, J=7.6 Hz, 1H), 7.03 (d, J=8.8 Hz, 2H), 3.88 (s, 3H). ESIMS (m/z) for C$_{17}$H$_{15}$N$_2$O$_2^+$ [M+H]$^+$: calculated 279.3, found 279.1.

Example 54-13c (E)-1-(4-methoxyphenyl)-3-(3-(4-methoxyphenyl)-1-phenyl-1H-pyrazol-4-yl) prop-2-en-1-one 13c (2.3 g, 77% yield) was synthesized by the same method as 1c. ESIMS (m/z) for C$_{26}$H$_{23}$N$_2$O$_3^+$ [M+H]$^+$: calculated 411.5, found 411.1.

Example 55-13d

3', 5-bis (4-methoxyphenyl)-1'-phenyl-3, 4-dihydro-1'H, 2H-3, 4'-bipyrazole 13d was synthesized by the same method as 1d. ESIMS (m/z) for C$_{26}$H$_{25}$N$_4$O$_2^+$ [M+H]$^+$: calculated 425.5, found 425.2.

Example 56-13e

Methyl 3-(3', 5-bis-(4-methoxyphenyl)-1'-phenyl-3, 4-dihydro-1'H, 2H-[3, 4'-bipyrazole]-2-carbonyl) benzoate 13e (58 mg, 41% yield) was synthesized by the same method as 1e. ESIMS (m/z) for C$_{35}$H$_{31}$N$_4$O$_5^+$ [M+H]$^+$: calculated 587.7, found 587.1.

Example 57-13

3-(3', 5-bis-(4-methoxyphenyl)-1'-phenyl-3, 4-dihydro-1'H, 2H-[3, 4'-bipyrazole]-2-carbonyl) benzoic acid 13 (31 mg, 54% yield) was synthesized by the same method as 1. $^1$H NMR (400 MHz, d$_6$-DMSO): δ 8.51 (s, 2H), 8.09 (t, J=8.8 Hz, 2H), 7.88 (d, J=8.0 Hz, 2H), 7.76 (d, J=8.0 Hz, 2H), 7.64 (d, J=8.4 Hz, 2H), 7.58 (t, J=7.6 Hz, 1H), 7.46 (t, J=7.6 Hz, 2H), 7.27 (d, J=7.2 Hz, 1H), 7.05 (d, J=8.4 Hz, 2H), 7.05 (d, J=8.4 Hz, 2H), 7.00 (d, J=8.4 Hz, 2H), 5.86-5.90 (m, 1H), 3.90-3.97 (m, 1H), 3.82 (s, 3H), 3.79 (s, 3H), 3.23-3.29 (m, 1H). $^{13}$C NMR (100 MHz, d$_6$-DMSO): (165.1, 161.5, 159.7, 155.6, 150.1, 139.9, 135.4, 133.9, 131.8, 131.0, 129.9, 129.9, 128.9, 128.3, 126.9, 126.5, 125.9, 124.2, 123.5, 118.6, 114.7, 114.5, 55.8, 55.7, 53.6, 42.3. ESIMS (m/z) for C$_{34}$H$_{29}$N$_4$O$_5^+$ [M+H]$^+$: calculated 573.6, found 573.2.

Scheme 5

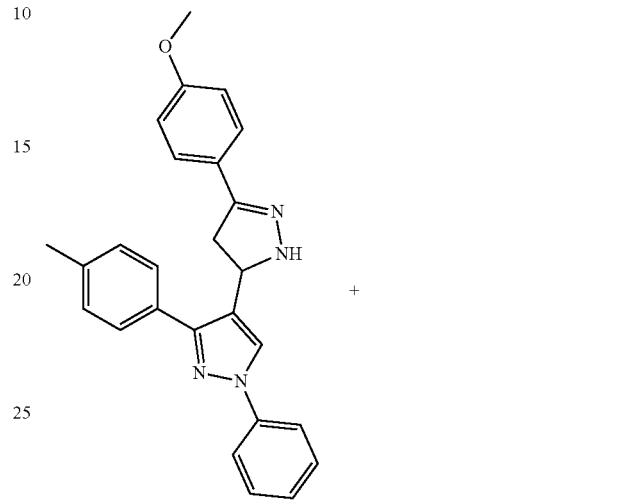

1d

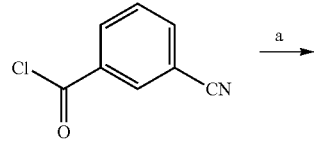

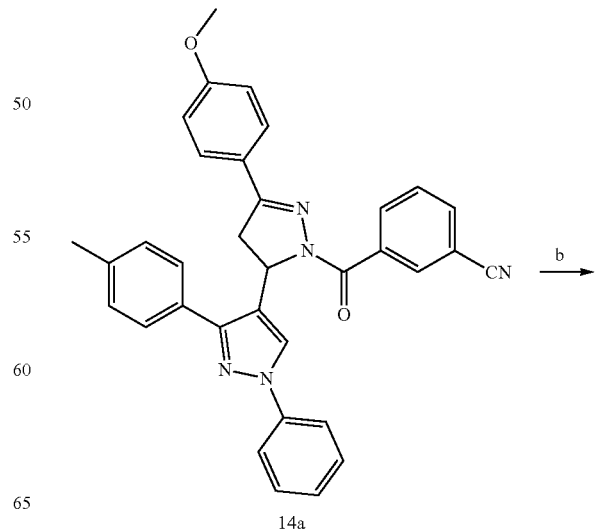

14a

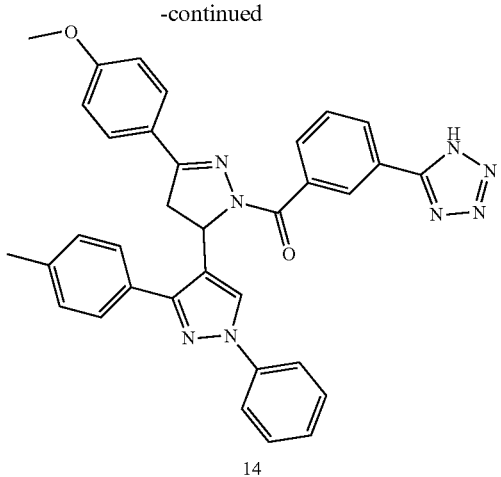

14

Scheme 5 depicts a route for synthesizing compound 14.

Example 58-14a 3-(5-(4-methoxyphenyl)-1'-phenyl-3'-(p-tolyl)-3,4-dihydro-1'H, 2H-[3, 4'-bipyrazole]-2-carbonyl) benzonitrile Using 1d as starting material, 14a (75 mg, 57% yield) was synthesized by the same method as 1e. ESIMS (m/z) for $C_{34}H_{28}N_5O_2^+$ [M+H]$^+$: calculated 538.6, found 538.3.

Example 59-14

(3-(1H-tetrazol-5-yl) phenyl) (5-(4-methoxyphenyl)-1'-phenyl-3'-(p-tolyl)-3, 4-dihydro-1'H, 2H-[3, 4'-bipyrazol]-2-yl) methanone A mixture of 14a (75 mg, 0.14 mmol), NaN$_3$ (90 mg, 1.39 mmol), CuSO$_4$.5H$_2$O (35 mg, 0.14 mmol), in DMSO (3 mL) in sealed tube was heated to 140° C. under N$_2$, and stirred for 5 hours and then cooled to rt. To the reaction mixture was filtered and the filtrate was purified by prep. HPLC to give 14 (22 mg, 27% yield). $^1$H NMR (400 MHz, CDCl$_3$): δ 8.64 (s, 1H), 8.09-8.21 (m, 2H), 7.90 (s, 1H), 7.50-7.59 (m, 7H), 7.29-7.33 (m, 2H), 7.11-7.19 (m, 3H), 6.84 (d, J=8.0 Hz, 2H), 6.11-6.14 (m, 1H), 3.79 (s, 3H), 3.61-3.68 (m, 1H), 3.12-3.17 (m, 1H), 2.29 (s, 3H). $^{13}$C NMR (100 MHz, CDCl$_3$): δ 161.8, 139.6, 138.1, 134.9, 132.7, 130.2, 129.9, 129.3, 128.6, 128.2, 126.5, 125.8, 124.2, 123.3, 121.6, 119.0, 114.2, 55.4, 41.6, 21.2. ESIMS (m/z) for $C_{34}H_{29}N_8O_2^+$ [M+H]$^+$: calculated 581.6, found 581.2.

Scheme 6

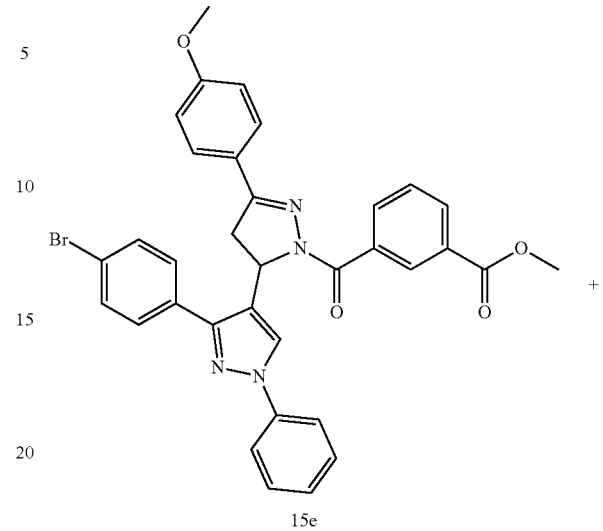

15e

+

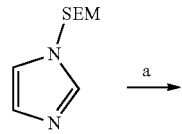

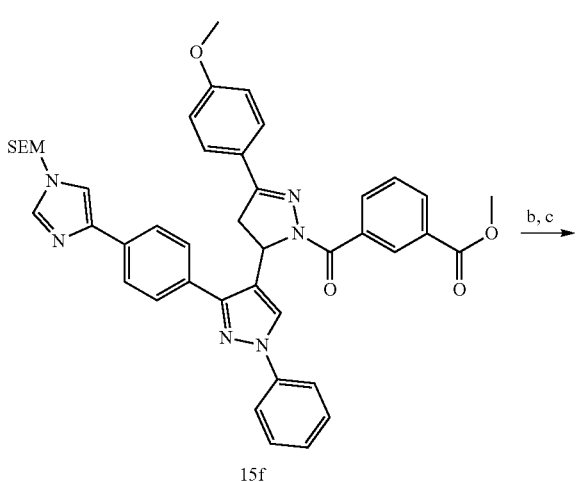

15f

-continued

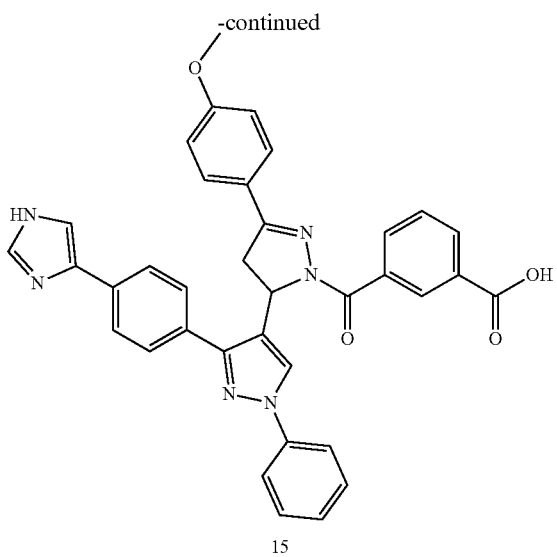

15

Scheme 5 depicts a route for synthesizing compound 15.

Example 60-15a (E)-1-(1-(4-bromophenyl) ethylidene)-2-phenylhydrazine 15a (5.1 g, 70% yield as orange solid) was synthesized by the same method as 1a. ESIMS (m/z) for $C_{14}H_{14}BrN_2^+$ [M+H]$^+$: calculated 289.0, 291.0 found 289.0, 291.0.

Example 61-15b 3-(4-bromophenyl)-1-phenyl-1H-pyrazole-4-carbaldehyde 15b (1.7 g, 75% yield) was synthesized by the same method as 1b. $^1$H NMR (400 MHz, CDCl$_3$): δ 10.04 (s, 1H), 8.53 (s, 1H), 7.76-7.80 (m, 4H), 7.64 (d, J=8.4 Hz, 2H), 7.53 (t, J=7.6 Hz, 2H), 7.41 (t, J=7.6 Hz, 1H). ESIMS (m/z) for $C_{16}H_{12}BrN_2O^+$ [M+H]$^+$: calculated 327.0, 329.0 found 327.0, 329.0.

Example 62-15c (E)-3-(3-(4-bromophenyl)-1-phenyl-1H-pyrazol-4-yl)-1-(4-methoxyphenyl) prop-2-en-1-one 15c (1.1 g, 79% yield) was synthesized by the same method as 1c. ESIMS (m/z) for $C_{25}H_{20}BrN_2O_2^+$ [M+H]$^+$: calculated 459.0, 461.0 found 459.0, 461.0.

Example 63-15d

3'-(4-bromophenyl)-5-(4-methoxyphenyl)-1'-phenyl-3, 4-dihydro-1'H, 2H-3, 4'-bipyrazole 15d (730 mg, 73% yield) was synthesized by the same method as 1d. ESIMS (m/z) for $C_{25}H_{22}BrN_4O^+$ [M+H]$^+$: calculated 473.1, 475.1 found 473.0, 475.1.

Example 64-15e

Methyl 3-(3'-(4-bromophenyl)-5-(4-methoxyphenyl)-1'-phenyl-3, 4-dihydro-1'H, 2H-[3, 4'-bipyrazole]-2-carbonyl) benzoate 15e (162 mg, 61% yield) was synthesized by the same method as 1e. $^1$H NMR (400 MHz, CDCl$_3$): δ 8.80 (s, 1H), 8.19 (t, J=7.2 Hz, 2H), 7.89 (s, 1H), 7.66-7.71 (m, 4H), 7.52-7.60 (m, 5H), 7.40 (t, J=7.2 Hz, 2H), 7.24-7.27 (m, 1H), 6.91 (t, J=8.4 Hz, 2H), 6.04 (d, J=7.6 Hz, 1H), 3.96 (s, 3H), 3.84 (s, 3H), 3.63-3.70 (m, 1H), 3.10-3.15 (m, 1H). ESIMS (m/z) for $C_{34}H_{28}BrN_4O_4^+$ [M+H]$^+$: calculated 635.1, 637.1 found 635.1, 637.1.

Example 65-15f

Methyl 3-(5-(4-methoxyphenyl)-1'-phenyl-3'-(4-(1-((2-(trimethylsilyl) ethoxy) methyl)-1H-imidazol-4-yl) phenyl)-3, 4-dihydro-1'H, 2H-[3, 4'-bipyrazole]-2-carbonyl) benzoate A mixture of 15e (100 mg, 0.16 mmol), 1-((2-(trimethylsilyl) ethoxy) methyl)-1H-imidazole (63 mg, 0.32 mmol), Pd (OAc) 2 (7 mg, 0.08 mmol), KOAc (31 mg, 0.32 mmol) in DMF (1 mL) was added in sealed tube and then heated to 140° C. under N$_2$ atm. After 5 h, the reaction mixture was cooled to room temperature and purified into water (5 mL). The mixture extracted with EA (5 mL*2). The organic phase was washed with brine, dried over Na$_2$SO$_4$, and filtered. The filtrate was concentrated. The residue was purified by prep. TLC (EA) to give 15f (48 mg, 40% yield). ESIMS (m/z) for $C_{43}H_{45}N_6O_5Si^+$ [M+H]$^+$: calculated 753.3, found 753.3.

Example 66-15

3-(3'-(4-(1H-imidazol-4-yl) phenyl)-5-(4-methoxyphenyl)-1'-phenyl-3, 4-dihydro-1'H, 2H-[3, 4'-bipyrazole]-2-carbonyl) benzoic acid A mixture of 15f (48 mg, 0.064 mmol) and LiOH·H$_2$O (27 mg, 0.64 mmol) in dioxane/water (1 mL/1 mL) was heated to 45° C. and stirred for 1 hours. The reaction mixture was cooled to room temperature and acidified to pH=6 by 1 M HCl. The reaction mixture was extracted with EA (10 mL*2). The organic phase was washed with brine, dried over Na$_2$SO$_4$, and filtered. The filtrate was concentrated. The residue was dissolved in DCM (1 mL). TFA (1 mL) was added the mixture. The resulting mixture was heated to 45° C. and stirred for 3 hours. The reaction mixture was concentrated and the residue was purified by prep. HPLC to give 15 (18 mg, 46% yield). $^1$H NMR (400 MHz, d$_6$-DMSO): δ 8.53-8.55 (m, 2H), 8.08-8.17 (m, 2H), 7.85-7.92 (m, 7H), 7.59-7.71 (m, 4H), 7.47 (t, J=8.0 Hz, 2H), 7.29 (t, J=7.6 Hz, 1H), 7.00 (d, J=8.8 Hz, 2H), 5.94-5.98 (m, 1H), 3.96-4.03 (m, 1H), 3.79 (s, 3H), 3.28-3.34 (m, 1H). $^{13}$C NMR (100 MHz, d$_6$-DMSO) δ167.4, 164.9, 161.5, 155.8, 150.0, 139.9, 135.6, 134.4, 131.8, 131.3, 131.1, 130.8, 129.9, 128.9, 128.7, 128.5, 127.0, 126.7, 125.0, 124.1, 123.8, 118.7, 114.7, 55.8, 53.7, 42.4. ESIMS (m/z) for $C_{36}H_{29}N_6O_4^+$ [M+H]$^+$: calculated 609.7, found 609.2.

Protein Expression and Purification

The plasmid of pET28a-Ca$_V$2.2β3 subunit was transformed into competent E. Coli BL21(DE3) strain. Culture was grown in LB medium at 37° C. to an OD600 of approximately 0.6 and then induced with 0.5 mM IPTG at 16° C. for 16 h. Cells were collected by centrifugation and lysed by microfluidizer in lysis buffer (phosphate buffer, pH 7.6, 2 mM DTT). The His-Ca$_V$β3 protein was purified at 4° C. using Ni-IMAC chromatography (His-Trap HP, GE Healthcare) and eluted with 500 mM imidazole in lysis buffer with a gradient method. After the fractions consisted of His-Ca$_V$β3 was combined and concentrated, the protein was further purified using size exclusion chromatography (Superdex 200 pg, GE Healthcare) in PBS with 2 mM DTT.

Label-Free Microscale Thermophoresis

Direct binding of compound 6 to Ca$_V$β3 was confirmed with label-free microscale thermophoresis (MST). Raw data was used to generate a binding curve that led to a dissociation (Kd) of 3.6±1.1 μM.

Site-Directed Mutagenesis

Compound 6 forms a salt bridge interaction with Arg-307 through a benzoic acid moiety. The removal of the charge, such as in compound 7, led to complete loss of inhibition of the CaVα1CaVβ3 interaction. Arg-307 was mutated to alanine. The resulting Ca$_V$β3 Arg-307-Ala mutant binds to CaVα1-$_{AID}$ with a Kd of 240±59 nM, a nearly 10-fold reduction.

Surface Biotinylation Assay

Cell-surface protein biotinylation and western blotting were performed. Briefly, HEKCa$_V$2.2 cells were treated with compound 6 or the vehicle (DMSO) for 48 hours. The surface proteins were biotinylated with 5 mM biotin-X-NHS (EMD Millipore, Billerica, MA) in PBS for 30 min at 4° C. After biotinylation, cells were quenched and washed with PBS containing 100 mM glycine. Then, cells were lysed in ice-cold RIPA buffer containing the Halt protease inhibitor cocktail (Thermo Fisher Scientific, Waltham, MA). The lysate was cleared by centrifugation, the pre-absorbed avidin-agarose beads were added, and the resulting suspension was rotated for 30 min at 4° C. The avidin-agarose beads were spun down and then washed 3 times with the complete lysis buffer. Proteins were eluted from the beads by incubating with SDS gel loading buffer supplemented with 1 mM DTT for 10 min at 70° C. The eluted proteins were separated using 10% SDS-polyacrylamide gel electrophoresis, transferred onto polyvinylidene difluoride membrane (PVDF) (Immun-Blot, Bio-Rad), and probed with the anti-Ca$_V$2.2-α1B antibody from Alomone Labs (1:1000 dilution; Israel, Cat. #: AC002) and the Na+, K+-ATPase antibody (1:1000 dilution; Cell Signaling, Cat. #3010). Compound 6 at 50 μM, significantly decreased surface presentation of the Ca$_V$2.2α1 subunit.

Patch Clamp Technique

The whole cell patch-clamp technique was used to record Ca$_V$2.2 currents in HEK-Ca$_V$2.2 cells and rat DRG neurons. HEK293 cells that stably expressed rat N-type CaV2.2α1B, rat CaVβ3, and rat β2δ-1 were utilized. Cells were grown in Dulbecco's modified Eagle's medium (DMEM) supplemented with 10% FBS, 50 units penicillin, 50 μg/ml streptomycin, 5 μg/ml blasticidin, 5 μg/ml hydromycin and 25 μg/ml zeozin at 37° C. in a humidified atmosphere of 95% air and 5% CO$_2$. For patch clamp experiments, HEK-Ca$_V$2.2 cells were plated on glass coverslips and were cultured for 24-48 h. All animal procedures were performed in accordance to the NIH guide and were approved by the Indiana University School of Medicine Institutional Animal Care and Use Committee. Young adult Sprague Dawley rats were anesthetized (3% isoflurane) and then decapitated. The spinal column was removed, cut open, and dorsal root ganglia were harvested from the Lumbar L4-L6 vertebral levels. The ganglia were incubated in DMEM containing collagenase (1 mg/ml, Worthington: LS04194) and protease (1 mg/ml, Worthington: LS02104) for 30-60 minutes, and DRG neurons were dissociated by triturating in DMEM supplemented with 10% FBS. The isolated DRG neurons were plated on glass coverslips coated with growth factor reduced Matrigel (Thermo Fisher Scientific, Waltham, MA) and were cultured in Eagle's minimum essential medium (Invitrogen, CA) supplemented with 0.2% BSA and 20 ng/ml NGF-2.5S (BD Biosciences, Bedford, MA) at 37° C. in a water-jacketed 5% CO$_2$ incubator overnight for the patch-clamp experiments.

Ca$_V$2.2 currents were recorded in HEK-Ca$_V$2.2 cells pre-treated with 10, 25, and 50 μM of compound 6 for 48 hours. The current densities obtained in the cells treated with 50 μM compound 6 were significantly decreased compared with vehicle DMSO group (IDMSO=−98.0±12.5 pA/pF, n=12 vs I6=−28.7±5.0 pA/pF, n=15, *p<0.001). G-V curves for CaV2.2 were shifted towards more positive potentials in HEK-Ca$_V$2.2 cells pretreated with compound 6 for 48 hours. The mean half-activation potential was greater in the cells compared to the control cells pretreated with DMSO for 48 hours (DMSO: 6.7±0.6 mV, n=14; compound 6: 9.4±1.2 mV, n=14, p<0.05). Conversely, acute application of 50 μM compound 6 did not affect Ca$_V$2.2 currents either in HEK-Ca$_V$2.2 cells or in rat DRG neurons, indicating that the compound does not inhibit the channel pore directly. Compound 2 did not affect the Ca$_V$2.2 currents amplitudes in HEK-Ca$_V$2.2 cells when it was used acutely or as a long-term treatment.

When activated by depolarizing pulses to 0 mV from a holding potential of −80 mV, the density of Ca$_V$2.2 currents were significantly smaller in HEK-Ca$_V$2.2 cells pretreated for 48 hours with 50 μM compound 14 than in cells treated with 50 μM compound 2 or DMSO (48 hours; compound 15: −11.1±2.4 pA/pF, n=12, compound 2: −79.2±8.2 pA/pF, n=9; DMSO: −74.8±7.0 pA/pF, n=15; p<0.001). The apparent IC50 for inhibition of Ca$_V$2.2 currents by compound 14 is 31 μM.

The CaV2.2 steady-state inactivation curves were significantly shifted towards more positive potentials in HEK-CaV2.2 cells pretreated for 48 hours with compound 14 (50 μM, V0.5, inact=−52.9±1.3 mV, p<0.005, n=10) compared with the control group (compound 2; 50 μM, V0.5, inact=−61.6±2.0 mV, n=10). The mean half-activation potential for Cav2.2 channels exhibited a more positive value in HEK-Cav2.2 cells pretreated for 48 hours with compound 14 (50 NM, V0.5, act=16.5±1.1 mV, p<0.001, n=12) compared with the controls (DMSO: V0.5, act=8.7±1.1 mV, n=12; compound 2: 50 μM, V0.5, act=8.5±1.4 mV, n=9).

No significant change in the mean half-activation voltage value was observed in patch-clamped HEK-Cav2.2 cells acutely treated with DMSO (Before: V0.5, act=9.1±1.6 mV; 5 min under DMSO: V0.5, act=6.8±3.3 mV, n=3, p>0.05). Conversely, a five-minute incubation with 50 μM compound 14 was sufficient to significantly shift the G-V curves of Cav2.2 towards more positive potentials (Before: V0.5, act=6.4±1.9 mV; 5 min under compound 15: V0.5, act=11.4±1.7 mV, n=7, p<0.01) indicating that the Cav2.2 channel requires a stronger depolarization to be activated in the presence of compound 14.

Animal Use

Pathogen-free, adult, female Sprague Dawley (weight at testing 150-200 g; Harlan-Sprague-Dawley, Indianapolis, IN) were housed in a climate-controlled room on a 12-hour light/dark cycle and were allowed to have food and water ad libitum. All procedures were approved by the Indiana University Animal Care and Use Committee and conformed to the guidelines of the National Institutes of Health (publication no. 80-23, 1966) for the use of laboratory animals. All behavioral experiments were conducted by experimenters blinded to the treatment conditions and compound identity. The experiments were replicated a minimum of 2 times with independent cohorts of animals.

For in vivo studies, the inventive compounds were freshly prepared saline (0.9%) on the day of the experiment. Morphine sulfate salt (Sigma-Aldrich, St. Louis, MO) was freshly prepared on the day of the experiment in saline. All drugs were dissolved in 1 mL solution and administered by intraperitoneal (i.p.) injections 1 h prior to all behavioral assays.

Plasma concentrations at various time points were determined using liquid chromatography tandem mass spectroscopy (LC-MS/MS). For intravenous (IV) administration, compound 14 was formulated as a solution at a final dose of 1 mg/kg. The elimination half-life of compound 14 was 0.29 hours. The Tmax in plasma was 0.083 hours, and the Cmax peak plasma concentration was 181.36 ng/ml. The AUC 0-t concentration was 57.99 ng/ml*h.

For oral gavage (PO) administration, compound 14 was formulated as a solution at a final dose of 10 mg/kg. Plasma concentrations at various time points were determined using LC-MS/MS. The elimination half-life of compound 14 was 1.99 hours. The Tmax in plasma was 1 hour, and the Cmax peak plasma concentration was 164.7 ng/ml. The AUC 0-t concentration was 635.555 ng/ml*h.

Acute Thermal Nociception in the Rat

To evaluate the PWT to thermal stimulation, the Hargreaves' plantar test apparatus (Ugo Basile, Varese, Italy) was used. Measurements of the withdrawal latency of the paw began after the rats were habituated to the testing environment (IR setting=70). The measurements were repeated four times, at 5 min intervals and the initial pair of measurements was not used. The averages of the three remaining pairs of measurements taken were employed as data.

A model of behavioral sensitivity using thermal stimulus was used to determine the acute analgesic properties of the compounds of the present invention. Systemic administration of compound 6 failed to elicit changes in the response latency at 1 or 10 mg/kg.

Neuropathic Pain Attenuation

The inventive compounds were assessed with the tibial nerve injury (TNI) model of neuropathic pain 28 days after surgery. Using isoflurane anesthesia (4% induction and 2% maintenance), the right sciatic nerve was isolated under aseptic surgical conditions by blunt dissection of the femoral biceps muscle and the tibial nerve was tightly ligated with 5-0 silk and transected distal to the ligation. Additional 2 to 3 mm of distal nerve stump was removed to prevent reinnervation by the proximal nerve. The overlying muscle and skin was then sutured in 2 separate layers. Sham-injured animals were subjected to all preceding procedures with the exception of ligation and transection. All animals were returned to the housing facility and allowed to survive for 28 d. Mechanical stimuli were applied with 7 filaments, each differing in the bending force delivered (10, 20, 40, 60, 80, 100, and 120 mN), and fitted with a flat tip and fixed diameter of 0.2 mm. The filaments were tested in the order of ascending force, with each filament delivered for 1 second. Withdrawal threshold was determined by sequentially increasing and analyzed with Hill equation was fitted to the function (Origin version 6.0; Microcal Software) relating the percentage of indentations eliciting a withdrawal to the force of indentation.

Before administration, all injured animals exhibited pronounced mechanical allodynia (33.1±5.9 mN; n=8-10) in response to von Frey hair stimulation of the injured hind paw, compared with pre-surgery levels, which averaged 68.7±3.7 mN (n=8-10). Pronounced attenuation of tactile hypersensitivity was observed at 1 h but not at 4 h after systemic administration of compound 6 (10 mg/kg, ip; 62.2±3.1 mN; n=16). Compound 6 dosing levels of 1 mg/kg and 0.1 mg/kg did not alter behavior at 1 or 4 hours. In contrast, systemic administration of morphine (5 mg/kg) and compound 2 (10 mg/kg, ip) were ineffective at reducing hypersensitivity, with levels averaging 32±2.6 mN (n=8). That PWT returned to baseline by 4 hours in compound 6-injected rats is consistent with the turnover of drug over this period. Rats 28 days after TNI exposed to compound 14 (0.1 mg/kg) significantly increased PWTs at both 1 and 24 hours post-injection compared to compound 6 and vehicle control.

Pharmacokinetics

PK profiles of compound 14 after intravenous and oral administration was performed in Kunming mice. Plasma concentrations were determined by liquid chromatography tandem mass spectroscopy. Summary of PK properties and plasma concentration measured 1 hour after intravenous or oral administration of 1 or 10 mg/kg compound 14.

Other variations or embodiments will be apparent to a person of ordinary skill in the art from the above-description. Thus, the foregoing embodiments are not to be construed as limiting the scope of the claimed invention.

What is claimed is:

1. A compound of Formula (1)

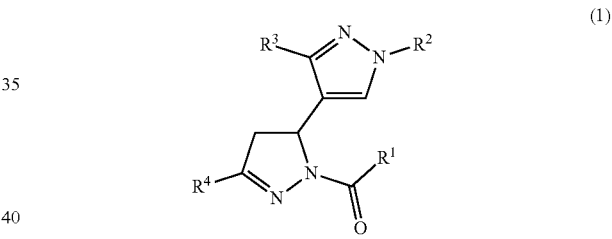

wherein
$R^1$ is selected from the group consisting of ($C_1$-$C_4$ alkyl)-$CO_2H$, —$CO_2H$ substituted phenyl, and tetrazole substituted phenyl;
$R^2$ is selected from the group consisting of phenyl, methoxy substituted phenyl, and pyridinyl;
$R^3$ is selected from the group consisting of ($C_1$-$C_3$ alkyl) substituted phenyl and halo substituted phenyl; and
$R^4$ is selected from the group consisting of alkoxy substituted phenyl and pyridyl substituted phenyl;
with the proviso that the compound of Formula (1) is not

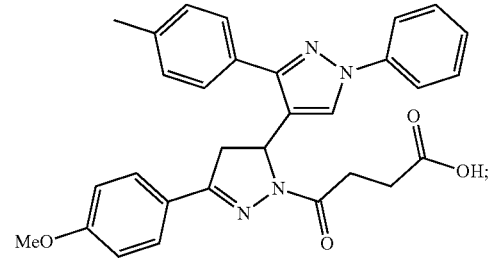

or a pharmaceutically acceptable salt thereof.

2. The compound or pharmaceutically acceptable salt thereof of claim 1, wherein $R^1$ is tetrazole substituted phenyl.

3. The compound or pharmaceutically acceptable salt thereof of claim 2, wherein $R^2$ is phenyl, or methoxy substituted phenyl.

4. The compound or pharmaceutically acceptable salt thereof of claim 2, wherein $R^2$ is phenyl.

5. The compound or pharmaceutically acceptable salt thereof of claim 1, wherein $R^3$ is methyl-phenyl or chloro-phenyl.

6. The compound or pharmaceutically acceptable salt thereof of claim 4, wherein $R^3$ is ($C_1$-$C_3$ alkyl) substituted phenyl.

7. The compound or pharmaceutically acceptable salt thereof of claim 1, wherein $R^4$ is methoxy-phenyl.

8. A compound selected from the group consisting of

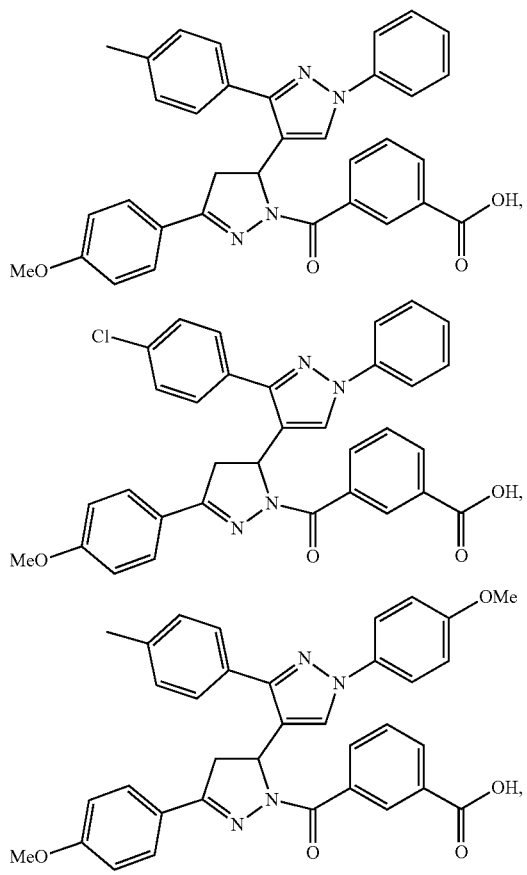
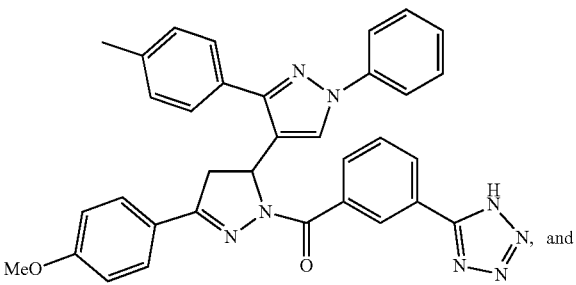
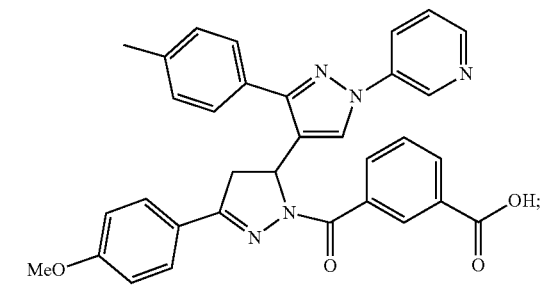

or a pharmaceutically acceptable salt thereof.

9. The compound of claim 8, selected from the group consisting of

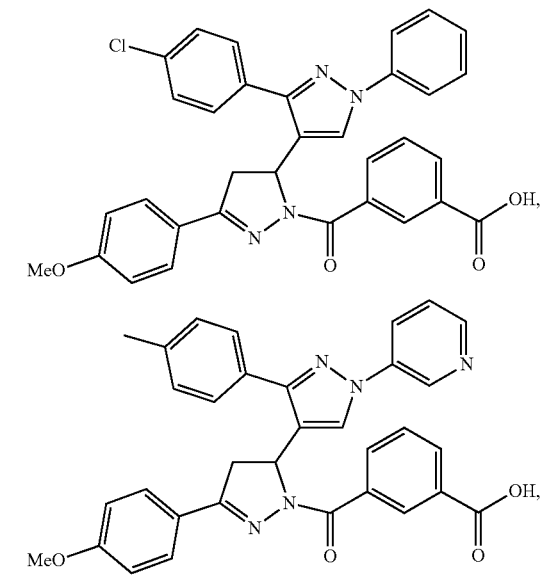
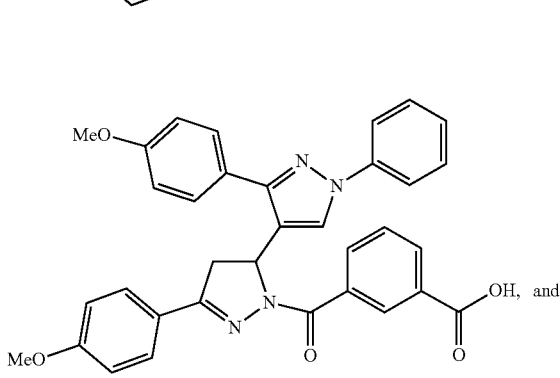

-continued

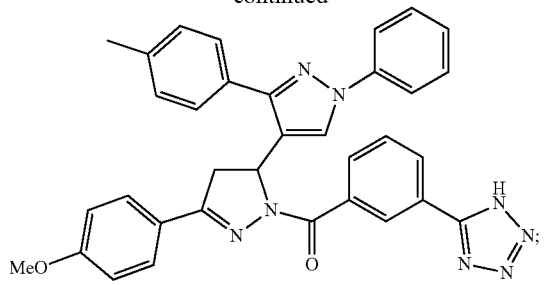

or a pharmaceutically acceptable salt thereof.

10. A compound of Formula (1)

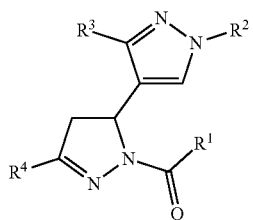

(1)

wherein:

R$^1$ is selected from the group consisting of —CO$_2$H substituted phenyl, and tetrazole substituted phenyl;

R$^2$ is selected from the group consisting of phenyl, methoxy substituted phenyl and pyridinyl;

R$^3$ is (C$_1$-C$_3$ alkyl) substituted phenyl and halo substituted phenyl; and R$^4$ is alkoxy substituted phenyl;

or a pharmaceutically acceptable salt thereof.

11. The compound of claim 10, wherein:

R$^1$ is tetrazole substituted phenyl;

R$^2$ is phenyl;

R$^3$ is methyl-phenyl; and

R$^4$ is methoxy-phenyl.

12. The compound of claim 10, wherein:

R$^1$ is tetrazole substituted phenyl;

R$^2$ is selected from the group consisting of phenyl, and methoxy substituted phenyl;

R$^3$ is (C$_1$-C$_3$ alkyl) substituted phenyl; and

R$^4$ is alkoxy substituted phenyl;

or a pharmaceutically acceptable salt thereof.

* * * * *